United States Patent
Iwasaki

(10) Patent No.: US 10,694,930 B2
(45) Date of Patent: Jun. 30, 2020

(54) ENDOSCOPE REPROCESSOR

(71) Applicant: OLYMPUS CORPORATION, Tokyo (JP)

(72) Inventor: Tomokazu Iwasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 108 days.

(21) Appl. No.: 16/026,487

(22) Filed: Jul. 3, 2018

(65) Prior Publication Data
US 2018/0325367 A1   Nov. 15, 2018

Related U.S. Application Data

(63) Continuation of application No. PCT/JP2017/006606, filed on Feb. 22, 2017.

(30) Foreign Application Priority Data

Jul. 29, 2016   (JP) ................ 2016-150313

(51) Int. Cl.
*A61B 1/12* (2006.01)
*A61L 2/24* (2006.01)
(Continued)

(52) U.S. Cl.
CPC .......... *A61B 1/123* (2013.01); *A61B 1/00057* (2013.01); *A61B 90/70* (2016.02);
(Continued)

(58) Field of Classification Search
CPC ............... A61B 1/123; G01N 27/4163; G01N 27/4175; G01N 2201/127
See application file for complete search history.

(56) References Cited

U.S. PATENT DOCUMENTS

2003/0062262 A1* 4/2003 Mansouri ............. G01N 33/492
                                                              204/400
2003/0190257 A1* 10/2003 Halstead ................ A61B 1/123
                                                              422/28
(Continued)

FOREIGN PATENT DOCUMENTS

CN         101664560 A      3/2010
EP       3 032 246 A1       6/2016
(Continued)

OTHER PUBLICATIONS

JP5160350B2 Machine Translation (Year: 2013).*
(Continued)

*Primary Examiner* — Spencer E Bell
(74) *Attorney, Agent, or Firm* — Scully, Scott, Murphy & Presser, P.C.

(57) ABSTRACT

An endoscope reprocessor includes: a concentration measurement chamber; a liquid concentrate supply unit; a diluent supply unit; a holding unit configured to hold a concentration sensor; a memory; and a processor configured to produce information on a temporary standard curve based on a first point at which a first concentration is associated with a sensor output value at measurement of concentration of liquid concentrate and a second point at which a second concentration is associated with a sensor output value at measurement of concentration of a practical use solution after dilution, calculate a deviation degree between a standard curve and the temporary standard curve, and determine whether the temporary standard curve is valid from the deviation degree.

10 Claims, 17 Drawing Sheets

(51) Int. Cl.
  *A61B 1/00*   (2006.01)
  *A61L 2/18*   (2006.01)
  *A61B 90/70*  (2016.01)
  *B08B 9/023*  (2006.01)
  *B08B 3/08*   (2006.01)

(52) U.S. Cl.
  CPC .................................... *A61L 2/18* (2013.01);
    *A61L 2/24* (2013.01); *B08B 9/023* (2013.01);
    *A61B 2090/701* (2016.02); *A61L 2202/14*
    (2013.01); *A61L 2202/15* (2013.01); *A61L*
    *2202/24* (2013.01); *B08B 3/08* (2013.01)

(56) References Cited

U.S. PATENT DOCUMENTS

2005/0079094 A1   4/2005   Mariotti et al.
2014/0326282 A1*  11/2014  Kawachi ................ A61B 1/121
                                                    134/99.1
2016/0302654 A1   10/2016  Ogawa

FOREIGN PATENT DOCUMENTS

| JP | H09236566 A | 9/1997 |
| JP | 5160350 B2 * | 3/2013 |
| JP | 5826982 B1 | 12/2015 |
| JP | 5911659 B1 | 4/2016 |
| WO | 2003077960 A1 | 9/2003 |

OTHER PUBLICATIONS

Extended Supplementary European Search Report dated Jun. 12, 2019 in European Patent Application No. 17 83 3727.5.
International Search Report dated May 30, 2017 issued in PCT/2017/006606.

* cited by examiner

ENDOSCOPE REPROCESSOR

CROSS REFERENCE TO RELATED APPLICATION

This application is a continuation application of PCT/JP2017/006606 filed on Feb. 22, 2017 and claims benefit of Japanese Application No. 2016-150313 filed in Japan on Jul. 29, 2016, the entire contents of which are incorporated herein by this reference.

BACKGROUND OF INVENTION

1. Field of the Invention

The present invention relates to an endoscope reprocessor.

2. Description of the Related Art

Conventionally, reprocessing such as cleaning and disinfecting of a contaminated endoscope has been performed by an endoscope reprocessor. The endoscope reprocessor performs reprocessing with medicinal solution having a predetermined concentration.

A concentration sensor is known as an apparatus configured to measure liquid concentration. Typically, calibration of a standard curve needs to be periodically performed for the concentration sensor.

For example, cleaning solution having a predetermined pH value is used to clean a pH sensor that is a concentration sensor disclosed in Japanese Patent Application Laid-Open Publication No. 9-236566 and calibrate the standard curve of the pH sensor.

SUMMARY OF THE INVENTION

An endoscope reprocessor according to an aspect of the present invention includes: a concentration measurement chamber; a liquid concentrate supply unit configured to supply liquid concentrate containing an examination object at a first concentration to the concentration measurement chamber; a diluent supply unit configured to supply diluent for diluting the liquid concentrate to the concentration measurement chamber to prepare practical use solution containing the examination object at a second concentration; a holding unit configured to hold a concentration sensor so that the concentration sensor is in contact with the liquid concentrate and the practical use solution; a memory configured to store information on standard curve of the concentration sensor; and a processor configured to produce information on a temporary standard curve based on a first point at which the first concentration is associated with a sensor output value at measurement of concentration of the liquid concentrate and a second point at which the second concentration is associated with a sensor output value at measurement of concentration of the practical use solution, calculate a deviation degree between the standard curve and the temporary standard curve, and determine whether the temporary standard curve is valid from the deviation degree.

An endoscope reprocessor according to another aspect of the present invention includes: a concentration measurement chamber; a liquid concentrate supply unit configured to supply liquid concentrate containing an examination object at a first concentration to the concentration measurement chamber; a diluent supply unit configured to supply diluent for diluting the liquid concentrate to the concentration measurement chamber to prepare practical use solution containing the examination object at a second concentration; a holding unit configured to hold a concentration sensor so that the concentration sensor is in contact with the liquid concentrate and the practical use solution; a reprocessing basin in which an endoscope is disposed; a first solution transfer unit configured to transfer the practical use solution to the reprocessing basin and cause the practical use solution to contact with the endoscope; a second solution transfer unit configured to transfer the practical use solution contacted with the endoscope to the concentration measurement chamber; a counter configured to count the number of times that the practical use solution is transferred to the reprocessing basin; a memory configured to store information on standard curve of the concentration sensor; and a processor configured to produce information on a temporary standard curve based on at least one of a first point at which the first concentration is associated with a sensor output value at measurement of concentration of the liquid concentrate and a second point at which the second concentration is associated with a sensor output value at measurement of concentration of the practical use solution, and based on a third point at which a third concentration obtained by subtracting $N \times x$ (x is a positive number) from the second concentration is associated with a sensor output value at measurement of concentration of the practical use solution transferred to the reprocessing basin N times (N is equal to or larger than one), calculate a deviation degree between the standard curve and the temporary standard curve, and determine whether the temporary standard curve is valid from the deviation degree.

An endoscope reprocessor according to another aspect of the present invention includes: a concentration measurement chamber; an examination target solution supply unit configured to supply examination target solution to the concentration measurement chamber; a holding unit configured to hold a concentration sensor so that the concentration sensor is in contact with the examination target solution; a reprocessing basin in which an endoscope is disposed; a first solution transfer unit configured to transfer the examination target solution to the reprocessing basin and cause the examination target solution to contact with the endoscope; a second solution transfer unit configured to transfer the examination target solution contacted with the endoscope to the concentration measurement chamber; a counter configured to count the number of times that the examination target solution is transferred to the reprocessing basin; a memory configured to store information on standard curve of the concentration sensor; and a processor configured to produce information on a temporary standard curve based on a fourth point at which a fourth concentration is associated with a sensor output value at measurement of concentration of the examination target solution transferred to the reprocessing basin N times (N is equal to or larger than zero), and based on a fifth point at which a fifth concentration obtained by subtracting $m \times y$ (y is a positive number) from the fourth concentration is associated with a sensor output value at measurement of concentration of the examination target solution transferred to the reprocessing basin N+m times (m is equal to or larger than one), calculate a deviation degree between the standard curve and the temporary standard curve, and determine whether the temporary standard curve is valid based on the deviation degree.

DETAILED DESCRIPTION OF THE PREFERRED EMBODIMENT(S)

Embodiments of the present invention will be described below with reference to the accompanying drawings.

(Configuration)

Figure 1:
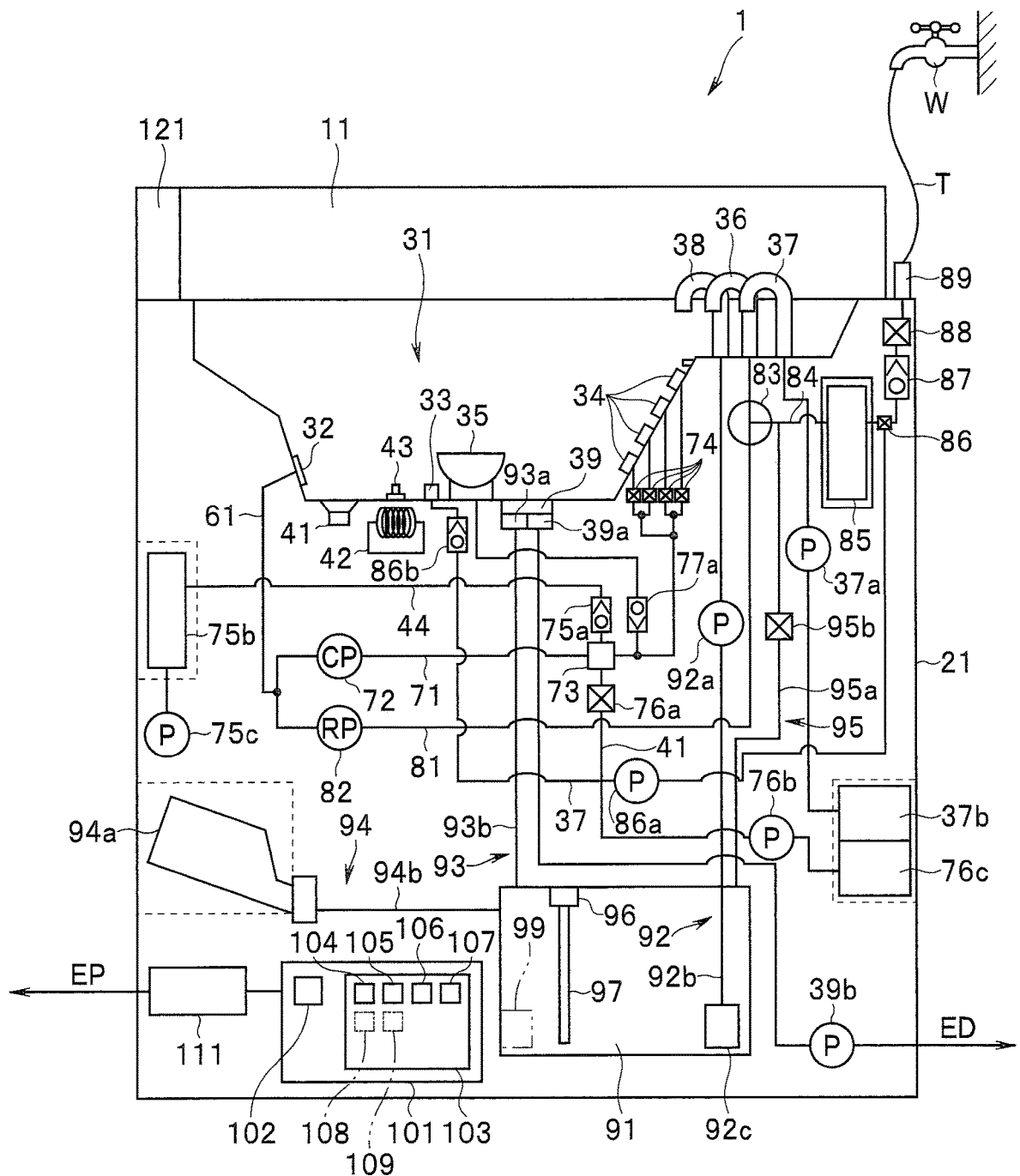
FIG. 1 is a diagram for description of the configuration of an endoscope reprocessor according to a first embodiment of the present invention.

FIG. 1 is a diagram for description of a configuration of an endoscope reprocessor 1 according to a first embodiment of the present invention. FIG. 1 omits illustration of any electric signal line.

The endoscope reprocessor 1 is an apparatus configured to perform reprocessing of, for example, a contaminated endoscope and a component or accessory of the endoscope. The reprocessing is not particularly limited but may be any of rinsing with water, cleaning that removes dirt such as organic substances, disinfecting that disables predetermined microorganisms, sterilization that removes or kills all microorganisms, or their combination.

The endoscope reprocessor 1 includes a top cover 11 and an apparatus body 21. The top cover 11 is provided above the apparatus body 21 and can be freely opened and closed. When the top cover 11 is opened, a reprocessing basin 31 is externally exposed.

The reprocessing basin 31 is formed in such a concave shape that an endoscope can be disposed inside the reprocessing basin 31 and liquid can be accumulated in the reprocessing basin 31. The reprocessing basin 31 includes circulation ports 32 and 33, an air/water feeding connector 34, a cleaning case 35, a circulation nozzle 36, a detergent nozzle 37, a medicinal solution nozzle 38, and a solution discharge port 39. The reprocessing basin 31 can output, by an ultrasound transducer 41, ultrasound to liquid accumulated in the reprocessing basin 31, can heat the liquid by a heater 42, and can sense the temperature of the liquid by a temperature sensing sensor 43.

The circulation port 32 is communicatively connected with a circulation conduit 61. The circulation conduit 61 bifurcates into a channel conduit 71 and a liquid transfer conduit 81, respectively.

The channel conduit 71 is communicatively connected with the air/water feeding connector 34 through a channel pump 72, a channel block 73, and a channel electromagnetic valve 74.

The channel block 73 is communicatively connected with an air pump 75c through an air feeding check valve 75a, an air feeding conduit 44, and an air filter 75b. The channel block 73 is also communicatively connected with an alcohol tank 76c through an alcohol electromagnetic valve 76a and an alcohol supply pump 76b. The channel conduit 71 bifurcates between the channel block 73 and the channel electromagnetic valve 74 and is communicatively connected with the cleaning case 35 through a relief valve 77a.

A connection tube which is not illustrated can be attached to the air/water feeding connector 34. The air/water feeding connector 34 is connected with the endoscope through the connection tube. The endoscope can be cleaned and disinfected by the air/water feeding connector 34 sending, to the endoscope, liquid taken in through the circulation port 32, gas fed by the air pump 75c, or alcohol transferred from the alcohol tank 76c.

The cleaning case 35 can house a component or accessory of the endoscope. In the cleaning case 35, the housed component or accessory of the endoscope can be cleaned and disinfected by liquid taken in through the circulation port 32 or gas fed by the air pump 75c.

The liquid transfer conduit 81 is communicatively connected with the circulation nozzle 36 through a liquid transfer pump 82 and a three-way electromagnetic valve 83. The three-way electromagnetic valve 83 is also communicatively connected with a water supply hose connection port 89 through a water supply conduit 84, a water supply filter 85, a three-way electromagnetic valve 86, a check valve 87, and a water supply electromagnetic valve 88. The three-way electromagnetic valve 86 is connected with a circulation port 33 through a pump 86*a* and a check valve 86*b*. The water supply hose connection port 89 is connected with a hydrant W through a tube T.

The circulation nozzle 36 supplies, to the reprocessing basin 31, any of liquid in the reprocessing basin 31 taken in through the circulation port 32, water supplied from the hydrant W, and liquid taken in through the circulation port 33.

The detergent nozzle 37 is communicatively connected with a detergent tank 37*b* through a detergent pump 37*a*. The detergent nozzle 37 supplies detergent in the detergent tank 37*b* to the reprocessing basin 31.

The medicinal solution nozzle 38 can supply medicinal solution accumulated in a medicinal solution tank 91 to the reprocessing basin 31. The medicinal solution nozzle 38 is communicatively connected with the medicinal solution tank 91 through a first solution transfer unit 92 to be described later.

Liquid in the reprocessing basin 31 can be discharged to the medicinal solution tank 91 through the solution discharge port 39. The solution discharge port 39 is communicatively connected with the medicinal solution tank 91 through a second solution transfer unit 93 to be described later. The solution discharge port 39 is communicatively connected with external liquid discharge means ED through a liquid discharge valve 39*a* and a liquid discharge pump 39*b* so that liquid in the reprocessing basin 31 can be discharged to the external liquid discharge means ED through the solution discharge port 39.

The medicinal solution tank 91, which serves as a concentration measurement chamber, can accumulate medicinal solution such as liquid concentrate or practical use solution. The medicinal solution tank 91 is connected with a liquid concentrate supply unit 94 and a diluent supply unit 95. The medicinal solution tank 91 includes a concentration sensor 97 held by a holding unit 96 so that the concentration of medicinal solution accumulated in the medicinal solution tank 91 can be measured.

The first solution transfer unit 92 includes a medicinal solution pump 92*a* and a medicinal solution conduit 92*b*. The first solution transfer unit 92 transfers medicinal solution to the reprocessing basin 31 and causes the medical solution to contact with the endoscope.

The second solution transfer unit 93 includes a medicinal solution recovery valve 93*a* and a medicinal solution recovery conduit 93*b*. The second solution transfer unit 93 transfers medicinal solution having contacted with the endoscope to the medicinal solution tank 91.

The liquid concentrate supply unit 94 can supply liquid concentrate containing an examination object at a first concentration to the medicinal solution tank 91. The liquid concentrate supply unit 94 includes a medicinal solution bottle 94*a* and a liquid concentrate supply conduit 94*b*. The medicinal solution bottle 94*a* can house a predetermined amount of liquid concentrate. When the medicinal solution bottle 94*a* is attached to the apparatus body 21, the medicinal solution bottle 94*a* is communicatively connected with the medicinal solution tank 91 through the liquid concentrate supply conduit 94*b*, and liquid concentrate housed in the medicinal solution bottle 94*a* is supplied to the medicinal solution tank 91 through the liquid concentrate supply conduit 94*b*. The amount of the liquid concentrate supplied to the medicinal solution tank 91 is defined by the capacity of the medicinal solution bottle 94*a*, but the present invention is not limited to the amount. For example, the amount of the liquid concentrate may be measured by a water level sensor 99 included in the medicinal solution tank 91.

The first concentration of the examination object is set in advance. For example, when the examination object is peracetic acid and the first concentration is 6%, the liquid concentrate is medicinal solution containing peracetic acid at 6%. The first concentration is not limited to 6%, and the examination object is not limited to peracetic acid.

The diluent supply unit 95 can supply diluent for diluting liquid concentrate to the medicinal solution tank 91 to prepare practical use solution containing the examination object at a second concentration. The diluent supply unit 95 includes a conduit 95*a* and an electromagnetic valve 95*b*. The conduit 95*a* is communicatively connected with the water supply conduit 84 and the medicinal solution tank 91. When the water supply electromagnetic valve 88 and the electromagnetic valve 95*b* are opened by a control unit 101, water supplied from the hydrant W is supplied to the medicinal solution tank 91 through the water supply conduit 84 and the conduit 95*a*. The amount of diluent supplied to the medicinal solution tank 91 is measured by the water level sensor 99 included in the medicinal solution tank 91, but the present invention is not limited to the amount. For example, the amount of diluent may be defined by a time period in which the electromagnetic valve 95*b* included in the diluent supply unit 95 is opened.

The second concentration of the examination object is set in advance. For example, the second concentration is 0.3%, and the diluent is water. The second concentration is not limited to 0.3%, and the diluent is not limited to water.

The holding unit 96 holds the concentration sensor 97 so that the concentration sensor 97 is in contact with medicinal solution containing the liquid concentrate and the practical use solution. The holding unit 96 may be installed at a position that allows a user to replace the concentration sensor 97.

The concentration sensor 97 is a sensor such as an electrochemical sensor. The concentration sensor 97 can measure the concentration of the examination object in medicinal solution in the medicinal solution tank 91. More specifically, the concentration sensor 97 changes a current value as a sensor output value through redox reaction in the medicinal solution in accordance with the concentration of the examination object in the medicinal solution. The concentration sensor 97 is connected with the control unit 101 and outputs, under control of the control unit 101, a current value as a sensor output value to the control unit 101. The outputting is not limited to a current value but, for example, a voltage value or a pulse may be outputted in accordance with the concentration of the examination object.

The medicinal solution tank 91 receives the liquid concentrate supplied from the liquid concentrate supply unit 94 and the diluent supplied from the diluent supply unit 95, and prepares practical use solution at a predetermined concentration from the liquid concentrate and the diluent. The prepared practical use solution is accumulated in the medicinal solution tank 91. The practical use solution accumulated in the medicinal solution tank 91 is sucked by the medicinal solution pump 92*a* through a suction filter 92*c* and supplied to the reprocessing basin 31 through the medicinal solution nozzle 38. After endoscope reprocessing ends, the practical use solution in the reprocessing basin 31 is discharged to the medicinal solution tank 91 through the solution discharge port 39. While the practical use solution is repeatedly used, the practical use solution mixes with any other liquid in the reprocessing basin 31, and reaction of the practical use solution proceeds. Accordingly, the concentration of the practical use solution gradually decreases.

The control unit 101 is provided in the apparatus body 21. The control unit 101 is connected with each component in the endoscope reprocessor 1 through an electric signal line, which is not illustrated, and controls operation of the respective components. The control unit 101 is connected with a power source apparatus 111. The power source apparatus 111 is connected with an external power source EP.

The control unit 101 includes a central processing unit (hereinafter referred to as a "CPU") 102, and a memory 103 including, for example, a ROM and a RAM. Each function of the control unit 101 is achieved by the CPU 102 reading and executing a computer program and data of each corresponding processing unit stored in the memory 103.

The memory 103 includes a standard curve storage unit 104 configured to store information on a standard curve Ls of the concentration sensor 97.

The memory 103 also stores a computer program for controlling operation of each component of the endoscope reprocessor 1, a computer program for standard curve production processing, and a computer program for measurement accuracy detection processing as well as computer programs that configure processing units such as a standard curve production unit 105 configured to produce information on the standard curve Ls of the concentration sensor 97 and a temporary standard curve Lc, a calculation unit 106 configured to calculate a deviation degree between the standard curve Ls and the temporary standard curve Lc, and a determination unit 107 configured to determine whether the temporary standard curve Lc is valid based on the deviation degree calculated by the calculation unit 106.

The apparatus body 21 includes a display unit 121. The display unit 121 is a display apparatus such as an LCD. The display unit 121 is connected with the control unit 101 and can perform display based on a control signal inputted from the control unit 101.

(Effects)
(Standard Curve Production Processing)

The following describes the standard curve production processing at the endoscope reprocessor 1 according to the first embodiment.

Figure 2:
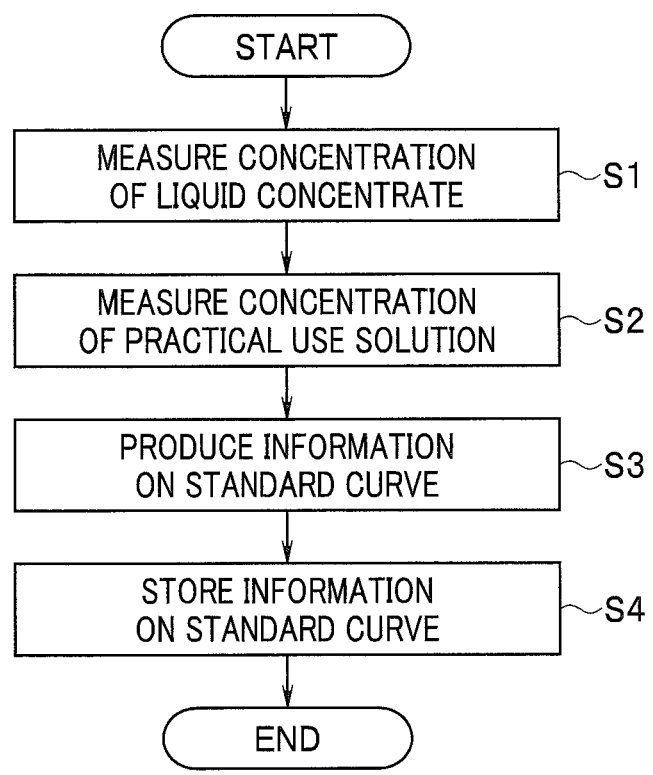
FIG. 2 is a flowchart illustrating a process of standard curve production processing at the endoscope reprocessor according to the first embodiment of the present invention.
Figure 3:
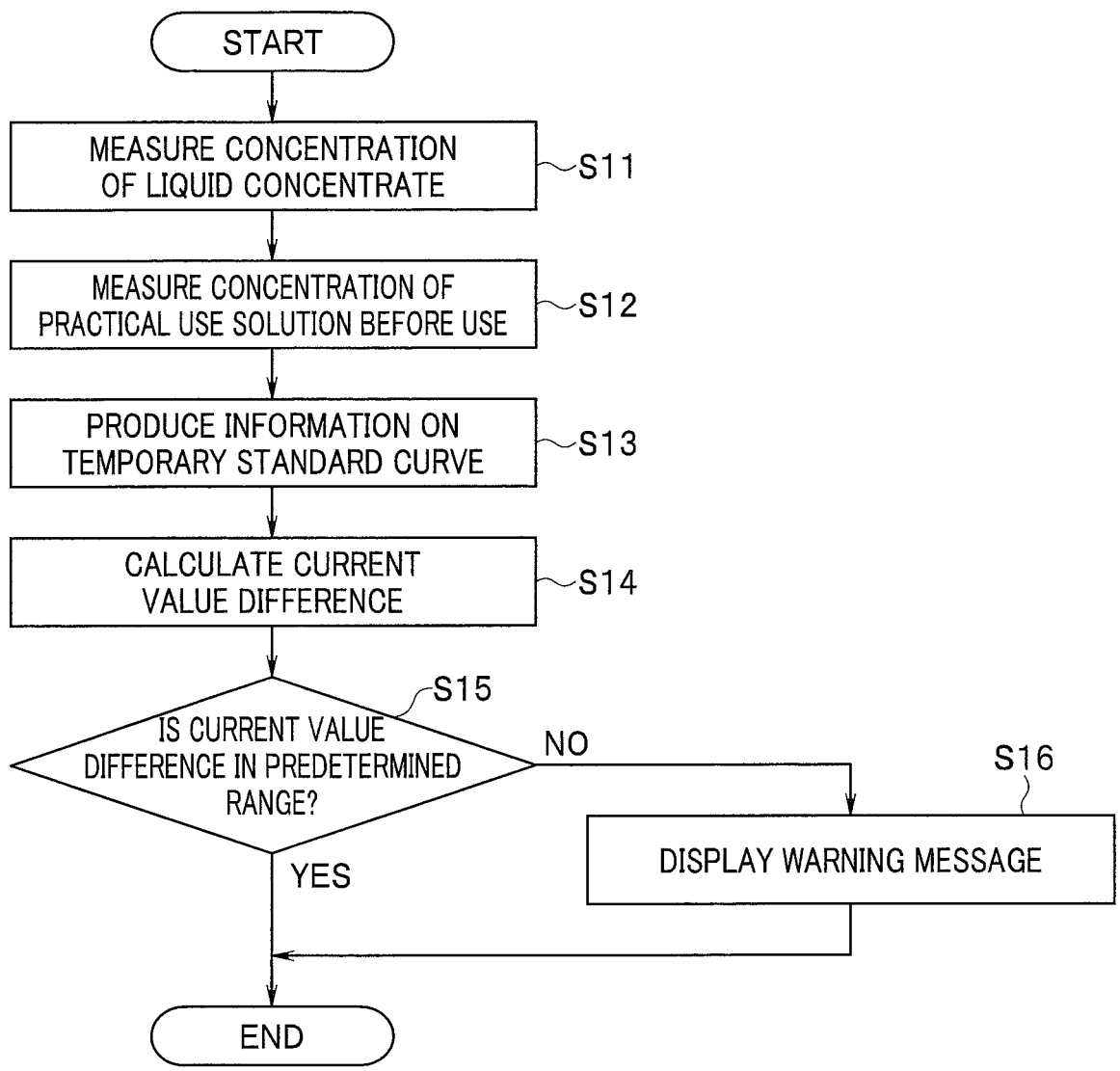
FIG. 3 is a flowchart illustrating a process of measurement accuracy detection processing at the endoscope reprocessor according to the first embodiment of the present invention.
Figure 4:
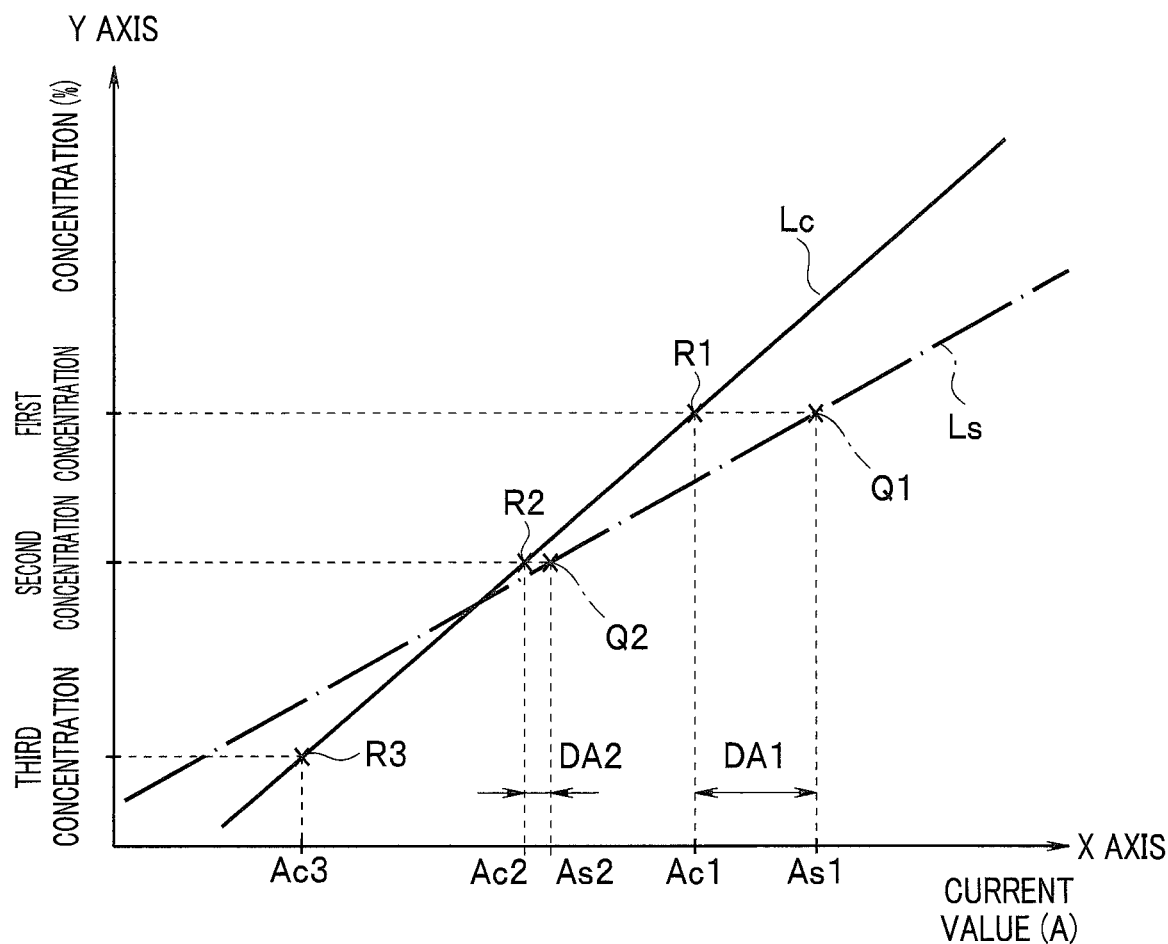
FIG. 4 is an explanatory diagram for description of a current value difference in the measurement accuracy detection processing at the endoscope reprocessor according to the first embodiment of the present invention.

FIG. 2 is a flowchart illustrating the process of the standard curve production processing at the endoscope reprocessor 1 according to the first embodiment of the present invention. FIG. 3 is a flowchart illustrating the process of the measurement accuracy detection processing at the endoscope reprocessor 1 according to the first embodiment of the present invention. FIG. 4 is an explanatory diagram for description of current value differences DA1 and DA2 in the measurement accuracy detection processing at the endoscope reprocessor 1 according to the first embodiment of the present invention.

The standard curve production processing is performed when the concentration sensor 97 is attached to the endoscope reprocessor 1, for example, before shipment from a factory or at replacement of the concentration sensor 97.

The concentration of liquid concentrate is measured (S1). At S1, liquid concentrate is supplied from the liquid concentrate supply unit 94 to the medicinal solution tank 91. More specifically, the medicinal solution bottle 94a is attached to the apparatus body 21 to supply, to the medicinal solution tank 91, the liquid concentrate containing the examination object at the first concentration in the medicinal solution bottle 94a. When the liquid concentrate is supplied into the medicinal solution tank 91, the concentration sensor 97 contacts with the liquid concentrate. The control unit 101 outputs a control signal for driving the concentration sensor 97 to the concentration sensor 97. Having received the control signal, the concentration sensor 97 measures the concentration of the liquid concentrate and outputs a current value as a sensor output value to the control unit 101.

The concentration of practical use solution is measured (S2). At S2, diluent is supplied from the diluent supply unit 95 to the medicinal solution tank 91. More specifically, the control unit 101 opens the water supply electromagnetic valve 88 and the electromagnetic valve 95b by outputting valve opening control signals to the water supply electromagnetic valve 88 and the electromagnetic valve 95b. When the water supply electromagnetic valve 88 and the electromagnetic valve 95b are opened, the diluent supplied from the hydrant W is supplied to the medicinal solution tank 91 through the water supply conduit 84 and the conduit 95a. After the supply of the diluent, practical use solution containing the examination object at the second concentration is prepared in the medicinal solution tank 91. The control unit 101 outputs a control signal for driving the concentration sensor 97 to the concentration sensor 97. Having received the control signal, the concentration sensor 97 measures the concentration of the practical use solution and outputs a current value as a sensor output value to the control unit 101.

Information on the standard curve Ls is produced (S3). The control unit 101 produces information including the standard curve Ls on an XY plane with an X axis representing the current value and a Y axis representing the concentration. More specifically, the control unit 101 produces the information including the standard curve Ls on the XY plane based on a measurement point Q1 at which the first concentration is associated with the current value as a sensor output value obtained at S1 and a measurement point Q2 at which the second concentration is associated with the current value as a sensor output value obtained at S2 (FIG. 4).

The information on the standard curve Ls is stored (S4). The control unit 101 stores the information on the standard curve Ls produced at S3 in the standard curve storage unit 104.

(Measurement Accuracy Detection Processing)

The following describes the measurement accuracy detection processing. The measurement accuracy detection processing is performed, for example, at concentration measurement when practical use solution is newly prepared.

S11 and S12 are same as S1 and S2, respectively, and thus description of S11 and S12 will be omitted.

Information on the temporary standard curve Lc is produced (S13). The control unit 101 produces information on the temporary standard curve Lc based on a first point R1 and a second point R2 as measurement points on the XY plane. Specifically, the temporary standard curve Lc is produced based on the first point R1 at which the first concentration is associated with a current value as a sensor output value at measurement of concentration of liquid concentrate and the second point R2 at which the second concentration is associated with a current value as a sensor output value at measurement of concentration of practical use solution.

The current value differences DA1 and DA2 are calculated (S14). The control unit 101 calculates the current value difference DA1 and the current value difference DA2 (FIG. 4). As indicated by equation (1) below, the current value difference DA1 is the difference between a current value Ac1 corresponding to the first concentration on the temporary standard curve Lc and a current value As1 corresponding to the first concentration on the standard curve Ls. As indicated by equation (2) below, the current value difference DA2 is the difference between a current value Ac2 corresponding to the second concentration on the temporary standard curve Lc and a current value As2 corresponding to the second concentration on the standard curve Ls.

$$DA1 = Ac1 - As1 \quad (1)$$

$$DA2 = Ac2 - As2 \quad (2)$$

Whether the current value differences DA1 and DA2 are each in a predetermined range is determined (S15). When the control unit 101 determines that the current value differences DA1 and DA2 calculated at S14 are each in the predetermined range (YES at S15), the processing ends. When the control unit 101 determines that at least one of the current value differences DA1 and DA2 is out of the predetermined range (NO at S15), the processing proceeds to S16, and the control unit 101 causes the display unit 121 to display a warning message. The predetermined range of the current value differences DA1 and DA2 is empirically or experimentally set in advance as a range that allows detection of decrease of the measurement accuracy at the concentration sensor 97.

At S16, the warning message is displayed. The control unit 101 outputs, to the display unit 121, a control signal for displaying the warning message, and causes the display unit 121 to display the warning message notifying the user of decrease of the measurement accuracy at the concentration sensor 97. After the warning message is displayed, the processing ends. The display of the warning message on the display unit 121 allows the user to notice the decrease of the measurement accuracy at the concentration sensor 97 and replace the concentration sensor 97.

The processing at S1 to S4 corresponds to the standard curve production processing according to the first embodiment.

The processing at S11 to S16 corresponds to the measurement accuracy detection processing according to the first embodiment.

The processing at S3 and S13 corresponds to processing at the standard curve production unit 105 according to the first embodiment.

The processing at S14 corresponds to processing at the calculation unit 106 according to the first embodiment.

The processing at S15 corresponds to processing at the determination unit 107 according to the first embodiment.

According to the above-described first embodiment, the endoscope reprocessor 1 includes the concentration sensor 97, measures the concentration of liquid concentrate and the concentration of practical use solution before use, produces the temporary standard curve Lc, and calculates the current value differences DA1 and DA2, which are each the deviation degree between the standard curve Ls and the temporary standard curve Lc, thereby detecting decrease of the measurement accuracy at the concentration sensor 97.

In the description of the first embodiment, as an example, the temporary standard curve Lc is produced from measurement points at each of which a concentration same as the concentration at production of the standard curve Ls is measured. However, the temporary standard curve Lc may be produced from measurement points at each of which a concentration different from the concentration at production of the standard curve Ls is measured, thereby calculating the deviation degree between the standard curve Ls and the temporary standard curve Lc.

Although described later in detail, information on the standard curve Ls does not necessarily need to be produced by the endoscope reprocessor 1.

Modification 1 of First Embodiment

Although the current value differences DA1 and DA2 are calculated as exemplary deviation degrees in the first embodiment, a gradient angle difference DO between the standard curve Ls and the temporary standard curve Lc may be calculated as a deviation degree.

Figure 5:
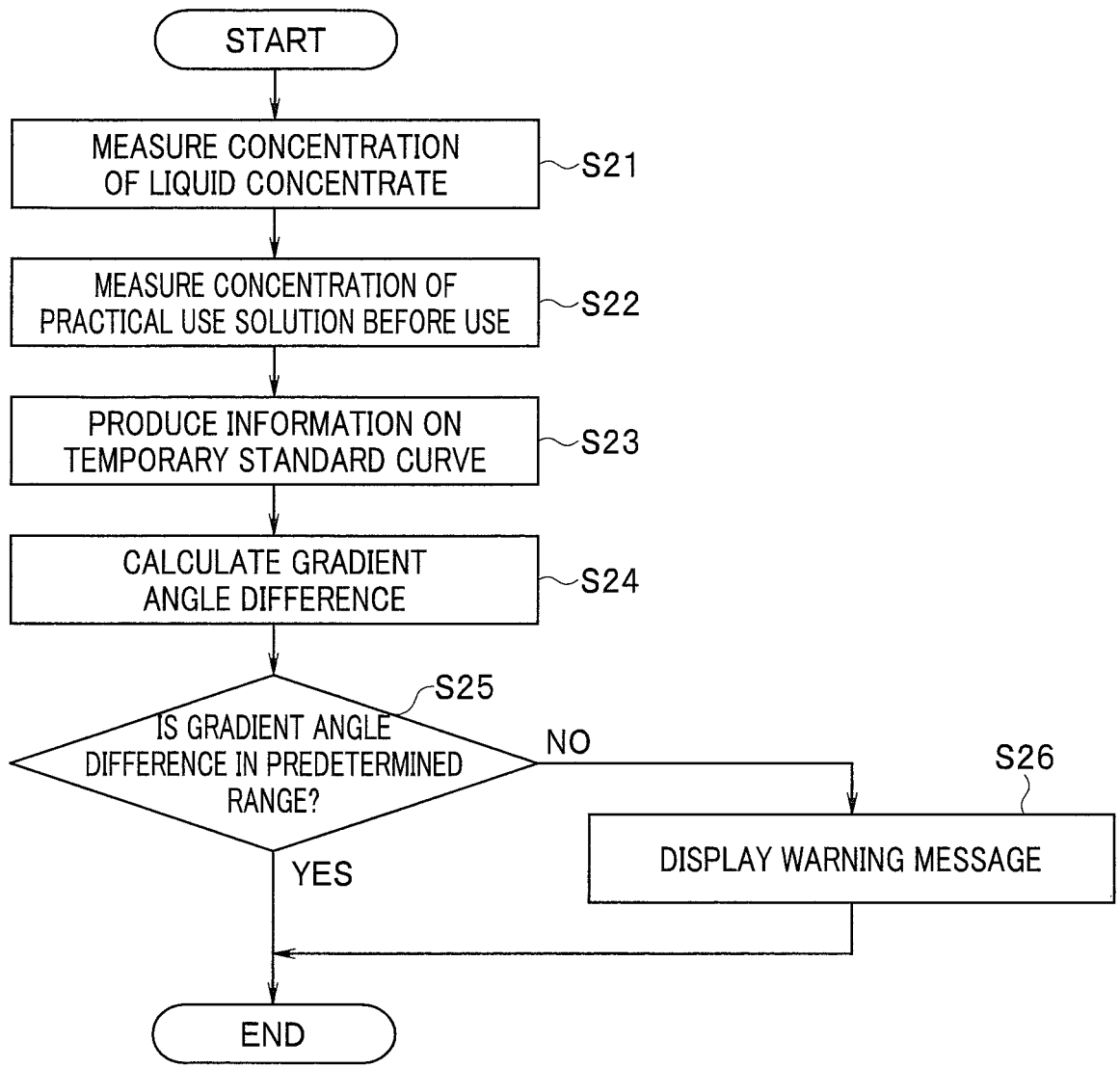
FIG. 5 is a flowchart illustrating a process of the measurement accuracy detection processing at the endoscope reprocessor according to Modification 1 of the first embodiment of the present invention.
Figure 6:
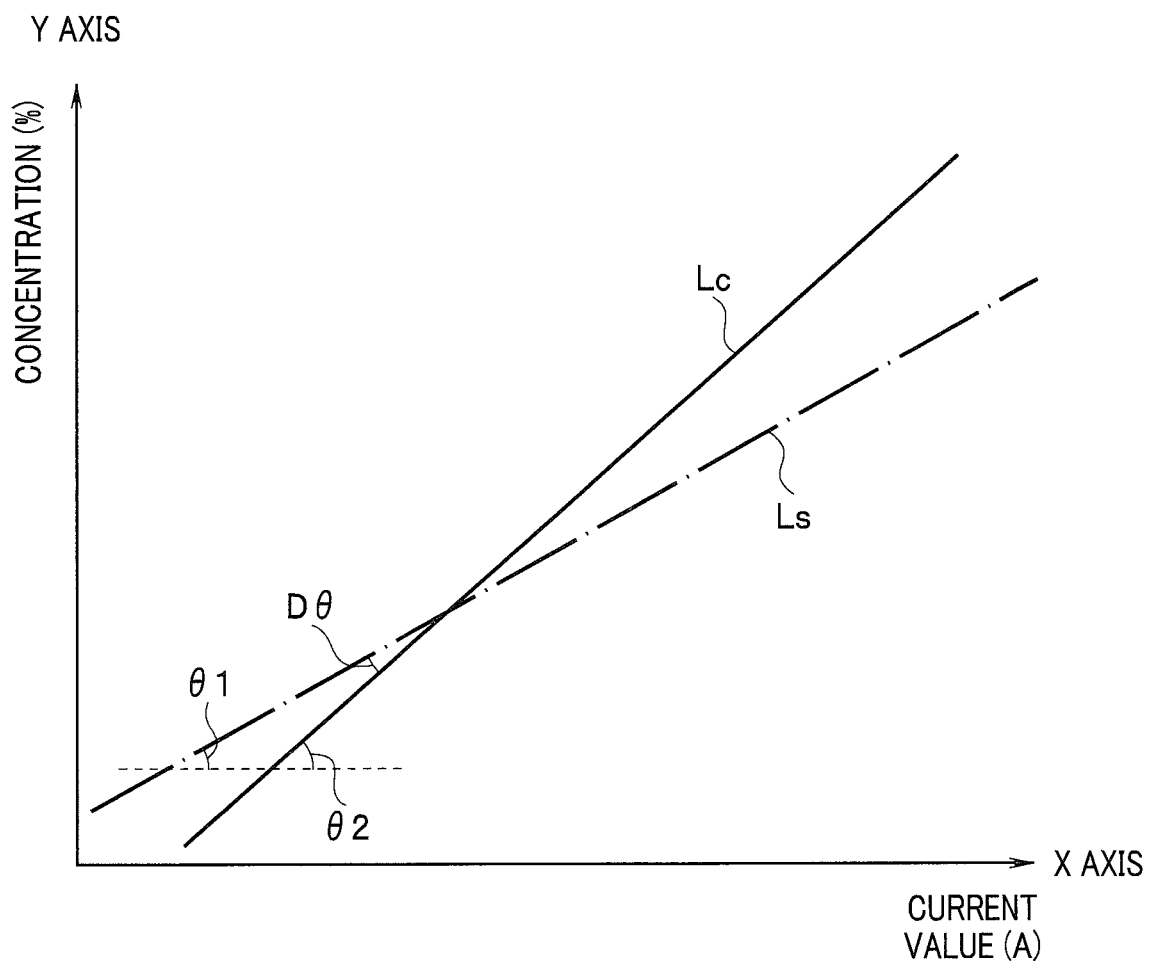
FIG. 6 is an explanatory diagram for description of a gradient angle difference in the measurement accuracy detection processing at the endoscope reprocessor according to Modification 1 of the first embodiment of the present invention.

FIG. 5 is a flowchart illustrating a process of the measurement accuracy detection processing at the endoscope reprocessor 1 according to Modification 1 of the first embodiment of the present invention. FIG. 6 is an explanatory diagram for description of the gradient angle difference DO in the measurement accuracy detection processing at the endoscope reprocessor 1 according to Modification 1 of the first embodiment of the present invention.

The following describes the measurement accuracy detection processing according to Modification 1 of the first embodiment. In the description of Modification 1 of the first embodiment, any component same as the component in the first embodiment is denoted by the same reference sign, and description of the component will be omitted.

Processing at S21 to S23 may be same as the processing at S1 to S3 or the processing at S11 to S13, and thus description of the processing will be omitted.

The gradient angle difference DO is calculated (S24). As illustrated in FIG. 6, the control unit 101 performs predetermined arithmetic processing to calculate a gradient angle $\theta1$ of the standard curve Ls and a gradient angle $\theta2$ of the temporary standard curve Lc produced at S23 on the XY plane. Subsequently, as indicated by equation (3) below, the control unit 101 calculates, as a deviation degree, the gradient angle difference DO that is the difference between the gradient angle $\theta1$ of the standard curve Ls and the gradient angle $\theta2$ of the temporary standard curve Lc. In other words, the control unit 101 calculates, through processing by the calculation unit 106, the deviation degree between the gradient $\theta1$ of the standard curve Ls and the gradient $\theta2$ of the temporary standard curve Lc.

$$D\theta = \theta1 - \theta2 \quad (3)$$

Whether the gradient angle difference DO is in a predetermined range is determined (S25). The control unit 101 determines whether the gradient angle difference D$\theta$ calculated at S24 is in the predetermined range. The gradient angle $\theta2$ of the temporary standard curve Lc is equal to the gradient angle $\theta1$ when no decrease of the measurement accuracy at the concentration sensor 97 occurs, and the gradient angle difference D$\theta$ from the gradient angle $\theta1$ increases in accordance with the decrease of the measurement accuracy at the concentration sensor 97. Thus, when the gradient angle difference D$\theta$ is in the predetermined range, it is determined that the temporary standard curve Lc produced at S23 is valid. When the gradient angle difference D$\theta$ is out of the predetermined range, it is determined that the temporary standard curve Lc is invalid. When the gradient angle difference DO calculated at S24 is in the predetermined range (YES at S25), the processing ends. When the gradient angle difference DO is out of the predetermined range (NO at S25), the processing proceeds to S26. The predetermined range of the gradient angle difference D$\theta$ is empirically or experimentally set in advance as a range that allows detection of decrease of the measurement accuracy at the concentration sensor 97.

Processing at S26 is same as the processing at S16, and thus description of the processing will be omitted.

The processing at S21 to S26 corresponds to the measurement accuracy detection processing according to Modification 1 of the first embodiment.

The processing at S24 corresponds to processing at the calculation unit 106 according to Modification 1 of the first embodiment.

The processing at S25 corresponds to processing at the determination unit 107 according to Modification 1 of the first embodiment.

Modification 2 of First Embodiment

Although the gradient angle difference DO is calculated as an exemplary deviation degree in Modification 1 of the first embodiment, an area DS of a region partitioned by the standard curve Ls and the temporary standard curve Lc in a predetermined current value range Ap may be calculated as a deviation degree.

Figure 7:
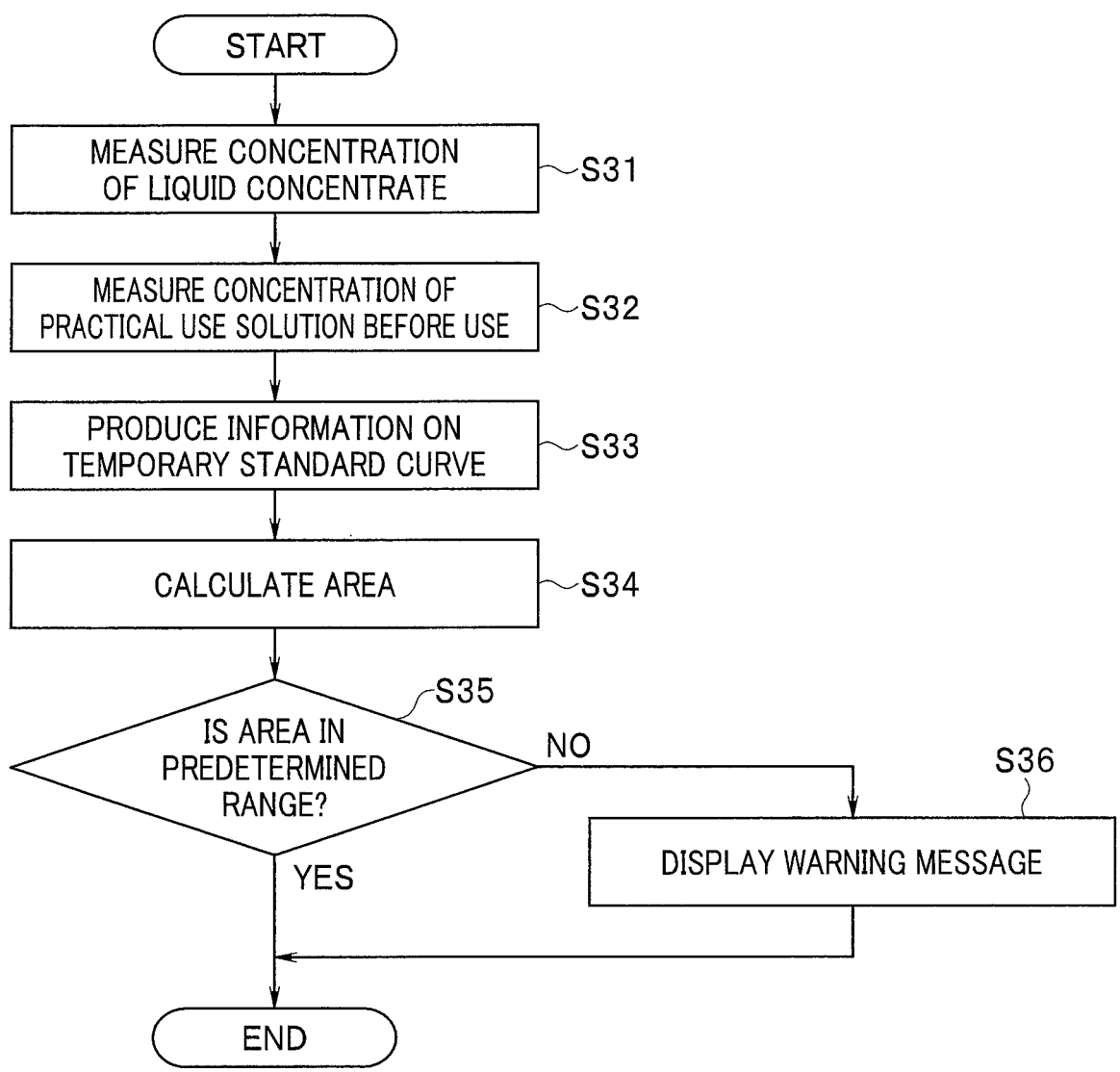
FIG. 7 is a flowchart illustrating a process of the measurement accuracy detection processing at the endoscope reprocessor according to Modification 2 of the first embodiment of the present invention.
Figure 8:
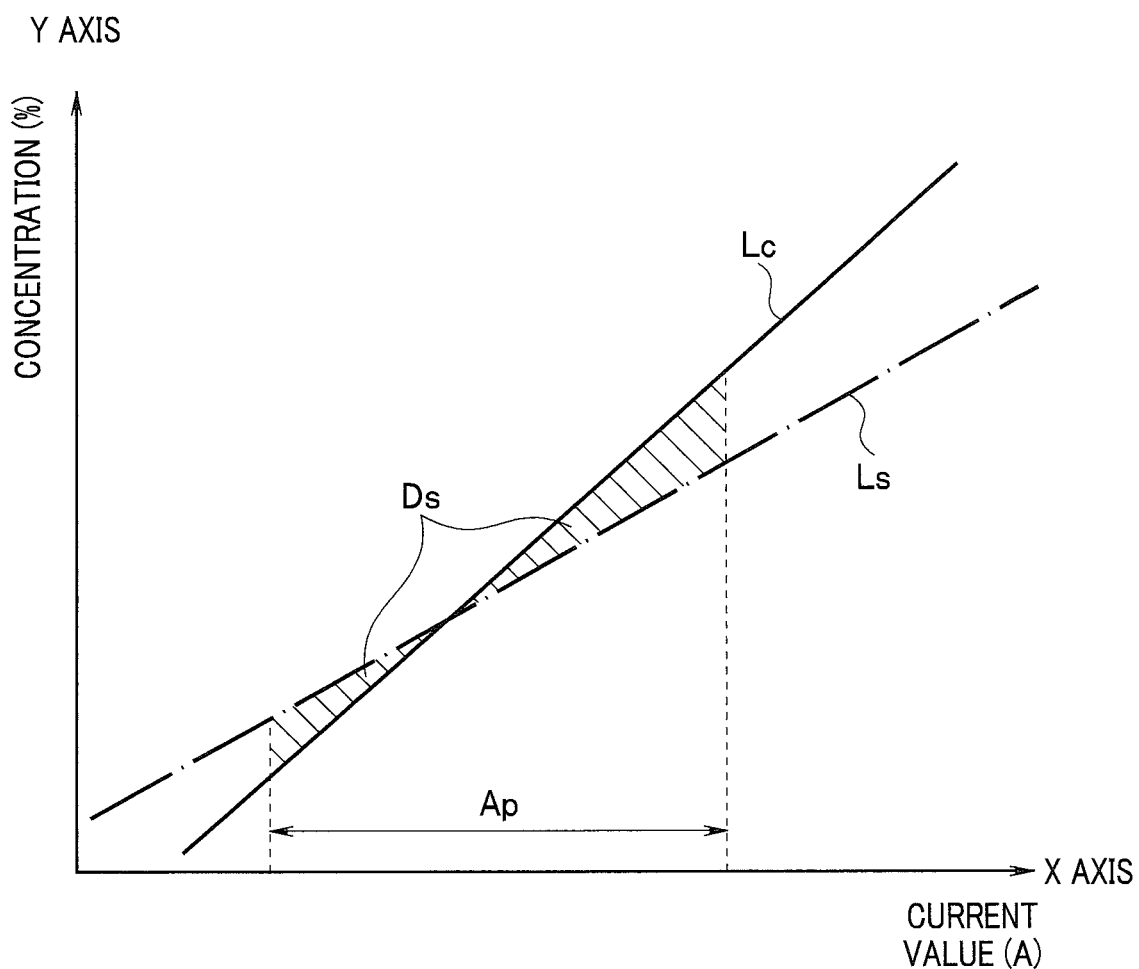
FIG. 8 is an explanatory diagram for description of area in the measurement accuracy detection processing at the endoscope reprocessor according to Modification 2 of the first embodiment of the present invention.

FIG. 7 is a flowchart illustrating the process of the measurement accuracy detection processing at the endoscope reprocessor 1 according to Modification 2 of the first embodiment of the present invention. FIG. 8 is an explanatory diagram for description of the area DS in the measurement accuracy detection processing at the endoscope reprocessor 1 according to Modification 2 of the first embodiment of the present invention.

The following describes the measurement accuracy detection processing according to Modification 2 of the first embodiment. In the description of Modification 2 of the first embodiment, any component same as the component in the first embodiment is denoted by the same identical reference sign, and description of the component will be omitted.

Processing at S31 to S33 may be same as any one of the processing at S1 to S3, the processing at S11 to S13, and the processing at S21 to S23, and thus description of the processing will be omitted.

The area DS is calculated (S34). As illustrated in FIG. 8, the control unit 101 performs predetermined arithmetic processing to calculate the area DS of the region partitioned by the standard curve Ls and the temporary standard curve Lc in the predetermined current value range Ap on the XY plane. The predetermined current value range Ap is set in advance as a range that defines a current value for calculating the area DS.

Whether the area DS is in a predetermined range is determined (S35). When the control unit 101 determines that the area DS calculated at S34 is in the predetermined range (YES at S35), the processing ends. When the control unit 101 determines that the area DS is out of the predetermined range (NO at S35), the processing proceeds to S36. The predetermined range of the area DS is empirically or experimentally set in advance to be a range that allows detection of decrease of the measurement accuracy at the concentration sensor 97.

Processing at S36 is same as the processing at S16 or the processing at S26, and thus description of the processing will be omitted.

The processing at S34 corresponds to processing at the calculation unit 106 according to Modification 2 of the first embodiment.

The processing at S35 corresponds to processing at the determination unit 107 according to Modification 2 of the first embodiment.

Second Embodiment

In the first embodiment, the temporary standard curve Lc is produced by measuring the concentration of liquid concentrate and the concentration of practical use solution before use, respectively, but may be produced by measuring the concentration of liquid concentrate and the concentration of practical use solution used a predetermined number N of times, respectively. The number N is equal to or larger than one.

Figure 9:
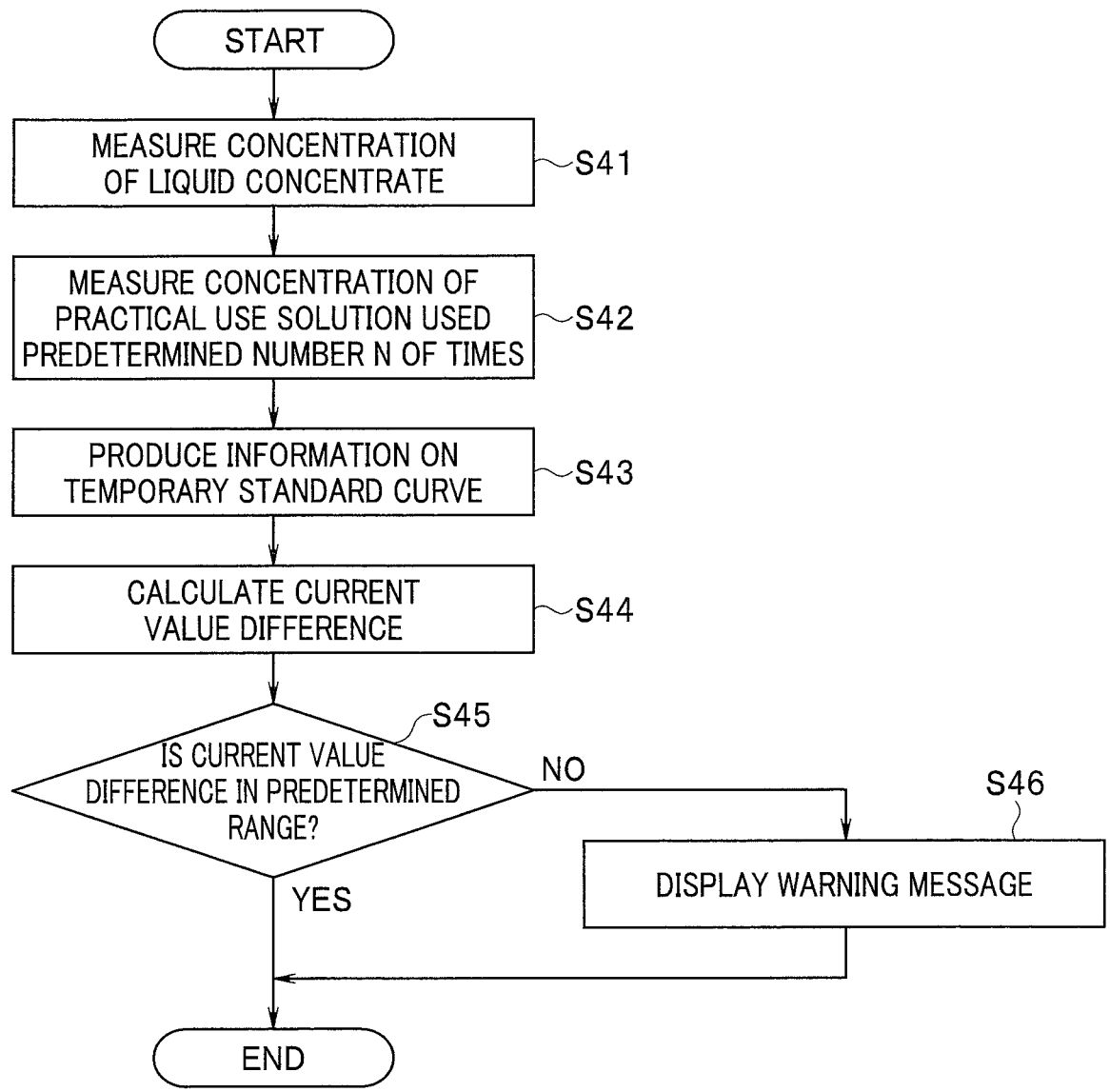
FIG. 9 is a flowchart illustrating a process of the measurement accuracy detection processing at the endoscope reprocessor according to a second embodiment of the present invention.

FIG. 9 is a flowchart illustrating the process of the measurement accuracy detection processing at the endoscope reprocessor 1 according to a second embodiment of the present invention. In the description of the second embodiment, any component same as the component in the first embodiment is denoted by the same reference sign, and description of the component will be omitted.

The control unit 101 includes a counting unit 108 (indicated by a dashed-double-dotted line in FIG. 1). The counting unit 108 can count the number of times that medicinal solution in the medicinal solution tank 91 is used in reprocessing. For example, the counting unit 108 counts the number of times that medicinal solution in the medicinal solution tank 91 is transferred to the reprocessing basin 31, by counting the number of times that the control unit 101 outputs a liquid transferring control signal to the medicinal solution pump 92a.

The following describes the measurement accuracy detection processing according to the second embodiment. In the description of the second embodiment, any component same as the component in the first embodiment and the modifications is denoted by the same reference sign, and description of the component will be omitted.

Processing at S41 may be same as any one of the processing at S1, the processing at S11, the processing at S21, and the processing at S31, and thus description of the processing will be omitted.

The concentration of practical use solution used the predetermined N of times is measured (S42). First, diluent is supplied from the diluent supply unit 95 to the medicinal solution tank 91 to prepare practical use solution containing the examination object at the second concentration. Subsequently, the practical use solution is transferred to the reprocessing basin 31 and used the predetermined N of times. The number of times of transfer to the reprocessing basin 31 is counted by the counting unit 108. Subsequently, the control unit 101 causes the concentration sensor 97 to measure the concentration of the practical use solution used the predetermined N of times, and acquires a current value Ac3 as a sensor output value from the concentration sensor 97.

Information on the temporary standard curve Lc is produced (S43). The control unit 101 produces the temporary standard curve Lc based on the first point R1 and a third point R3 on the XY plane. The third point R3 is a measurement point at which a third concentration is associated with the current value Ac3 as a sensor output value obtained at S42 (FIG. 4).

The third concentration is the concentration of practical use solution used the predetermined N of times. The third concentration is calculated by equation (4) below. In equation (4) below, C3(%) represents the third concentration, N (times) represents the predetermined number of times of transfer to the reprocessing basin 31, C2(%) represents the second concentration, and x (%) represents the amount of decrease of the concentration of practical use solution used once.

$$C3(\%)=C2(\%)-N(\text{times})\times x(\%) \qquad (4)$$

For example, when the second concentration is 0.3(%), the amount of decrease of the concentration of practical use solution used once is 0.005(%), and the number of times of transfer to the reprocessing basin 31 is 10 (times), the third concentration is 0.25(%).

Processing at S44 to S46 may be same as any one of the processing at S14 to S16, the processing at S24 to S26, and the processing at S34 to S36, and thus description of the processing will be omitted.

Accordingly, in the second embodiment, the standard curve production unit 105 can produce information on the temporary standard curve Lc based on the third point R3 at which the third concentration obtained by subtracting N×x (x is a positive number) from the second concentration is associated with the current value Ac3 at measurement of the concentration of medicinal solution transferred to the reprocessing basin 31 the predetermined N (N is equal to or larger than one) of times.

The processing at S41 to S46 corresponds to the measurement accuracy detection processing according to the second embodiment.

The processing at S43 corresponds to processing at the standard curve production unit 105 according to the second embodiment.

According to the above-described second embodiment, the endoscope reprocessor 1 can detect decrease of the measurement accuracy at the concentration sensor 97 by measuring, by the concentration sensor 97, the concentration of liquid concentrate and the concentration of practical use solution used the predetermined N of times. In the above-described example, the temporary standard curve Lc is produced based on the first point R1 associated with the first concentration and the third point R3 associated with the third concentration. However, the temporary standard curve Lc may be produced based on the second point R2 associated with the second concentration and the third point R3 associated with the third concentration, or may be produced based on the first point R1, the second point R2, and the third point R3.

Third Embodiment

In the endoscope reprocessor 1, the concentration of liquid concentrate and the concentration of practical use solution are measured, respectively, in the first and second embodiments and the modifications of the embodiments, but the concentration of practical use solution used without dilution may be measured.

Figure 10:
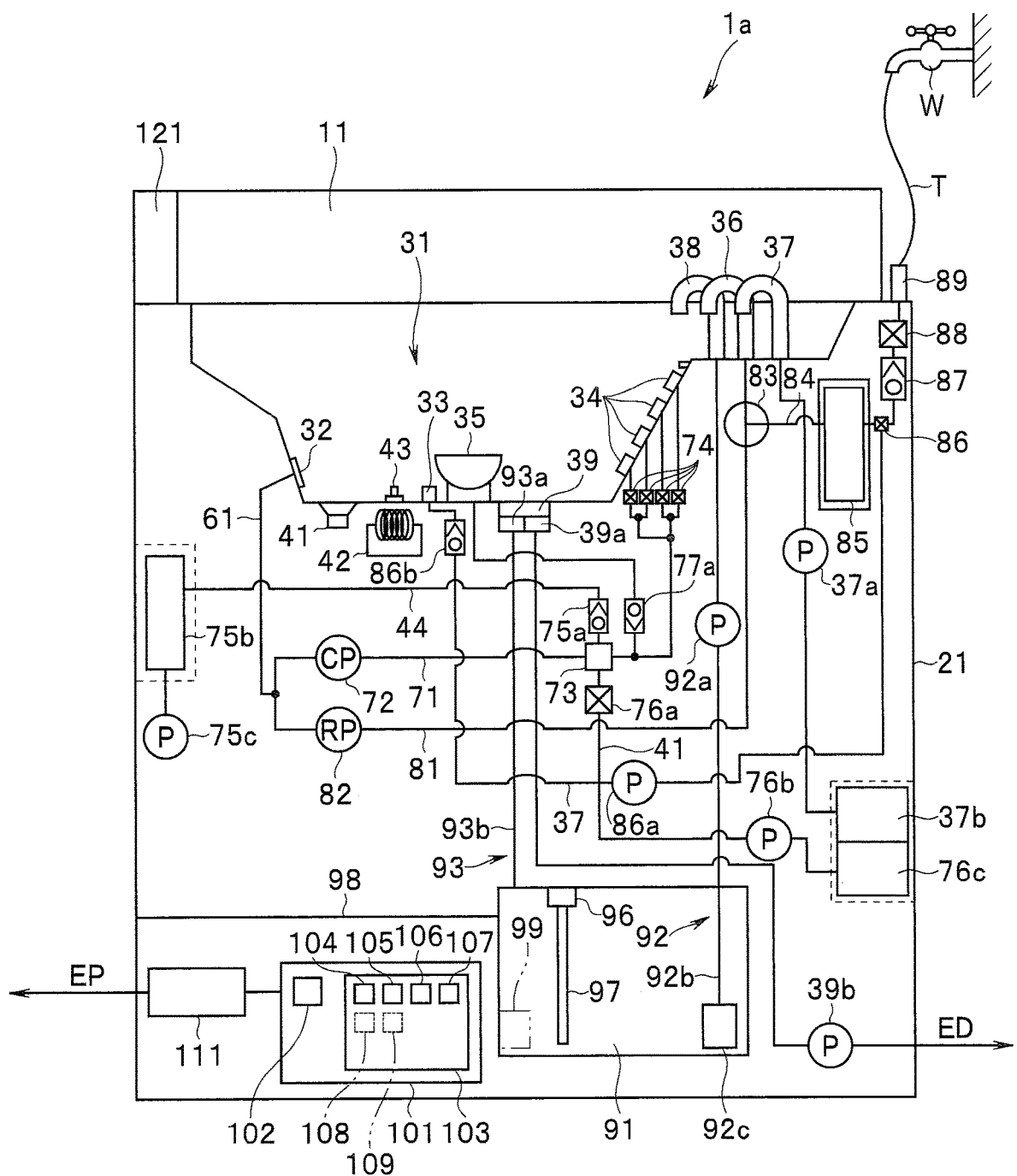
FIG. 10 is a diagram for description of a configuration of an endoscope reprocessor according to a third embodiment of the present invention.
Figure 11:
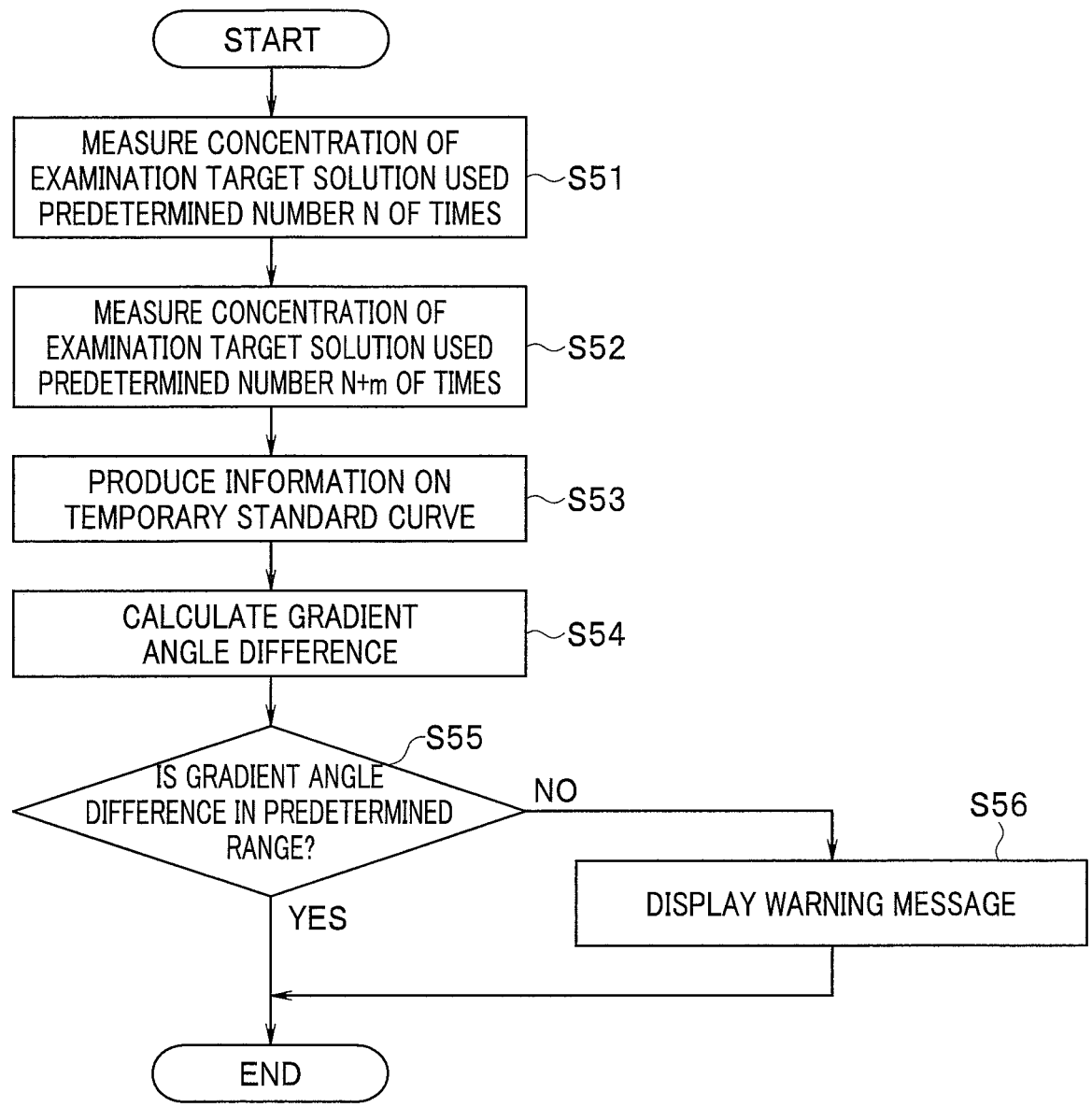
FIG. 11 is a flowchart illustrating a process of a measurement accuracy detection processing at the endoscope reprocessor according to the third embodiment of the present invention.

FIG. 10 is a diagram for description of the configuration of an endoscope reprocessor 1a according to a third embodiment of the present invention. FIG. 11 is a flowchart illustrating the process of the measurement accuracy detection processing at the endoscope reprocessor 1a according to the third embodiment of the present invention.

The following describes the endoscope reprocessor 1a according to the third embodiment. In the description of the third embodiment, any component same as the component in the first and second embodiments and the modifications of the embodiments is denoted by the same reference sign, and description of the component will be omitted.

In the third embodiment, the concentration of practical use solution used without dilution is measured.

The endoscope reprocessor 1a includes an examination target solution supply unit 98 configured to supply examination target solution to the medicinal solution tank 91 as a concentration measurement chamber. The examination target solution supply unit 98 can supply practical use solution as examination target solution to the medicinal solution tank 91.

The following describes the measurement accuracy detection processing according to the third embodiment.

The concentration of the examination target solution used the predetermined N of times is measured (S51). First, the examination target solution supply unit 98 supplies the examination target solution to the medicinal solution tank 91. Subsequently, the examination target solution is transferred to the reprocessing basin 31 and used the predetermined N of times. The number of times of transfer to the reprocessing basin 31 is counted by the counting unit 108. Subsequently, the control unit 101 causes the concentration sensor 97 to measure the concentration of the examination target solution, and acquires a current value as a sensor output value from the concentration sensor 97.

The concentration of the examination target solution used a predetermined number N+m of times is measured (S52). The examination target solution is used the predetermined N of times at S51, and then further used a predetermined number m of times. The control unit 101 causes the concentration sensor 97 to measure the concentration of the examination target solution, and acquires a current value as a sensor output value from the concentration sensor 97. The number m is equal to or larger than one.

Information on the temporary standard curve Lc is produced (S53). The control unit 101 produces information on the temporary standard curve Lc based on a fourth point and a fifth point on the XY plane. The fourth point is a measurement point at which a fourth concentration is associated with the current value as a sensor output value obtained at S51. The fifth point is a measurement point at which a fifth concentration is associated with the current value as a sensor output value obtained at S52.

The fourth concentration is calculated by equation (5) below. In equation (5), C4(%) represents the fourth concentration, N (times) represents the predetermined number of times of transfer to the reprocessing basin 31, which is equal to or larger than zero, C0(%) represents the concentration of the examination target solution before use, and y (%) represents the amount of decrease of the concentration of the examination target solution used once.

$$C4(\%) = C0(\%) - N(\text{times}) \times y(\%) \tag{5}$$

The fifth concentration is calculated by equation (6) below. In equation (6), C5(%) represents the fifth concentration, m (times) represents the predetermined number of times of transfer to the reprocessing basin 31, which is equal to or larger than one, C4(%) represents the fourth concentration, and y (%) represents the amount of decrease of the concentration of the examination target solution used once.

$$C5(\%) = C4(\%) - m(\text{times}) \times y(\%) \tag{6}$$

Accordingly, the control unit 101 can produce, through processing by the standard curve production unit 105, the temporary standard curve Lc based on the fourth point at which the fourth concentration is associated with a current value as a sensor output value at measurement of the concentration of the examination target solution transferred to the reprocessing basin 31 the predetermined N of times (N is equal to or larger than zero), and based on the fifth point at which the fifth concentration obtained by subtracting m×y from the fourth concentration is associated with a current value as a sensor output value at measurement of concentration of the examination target solution transferred to the reprocessing basin 31 the predetermined number N+m of times (m is equal to or larger than one).

Processing at S54 to S56 is same as the processing at S24 to S26, and thus description of the processing will be omitted.

The processing at S51 to S56 corresponds to the measurement accuracy detection processing according to the third embodiment.

The processing at S53 corresponds to processing at the standard curve production unit 105 according to the third embodiment.

According to the above-described third embodiment, the endoscope reprocessor 1a can detect decrease of the measurement accuracy at the concentration sensor 97 by measuring, by the concentration sensor 97, the concentration of the examination target solution used the predetermined N of times and the concentration of the examination target solution used the predetermined number N+m of times.

In the third embodiment, when the number N is set to be zero, the concentration of the examination target solution before use and the concentration of the examination target solution used the predetermined number m of times are measured to detect decrease of the measurement accuracy at the concentration sensor 97.

Modification 1 of Third Embodiment

In the third embodiment, the concentration of practical use solution used without dilution is measured, but the concentration of practical use solution used with dilution may be measured.

Figure 12:
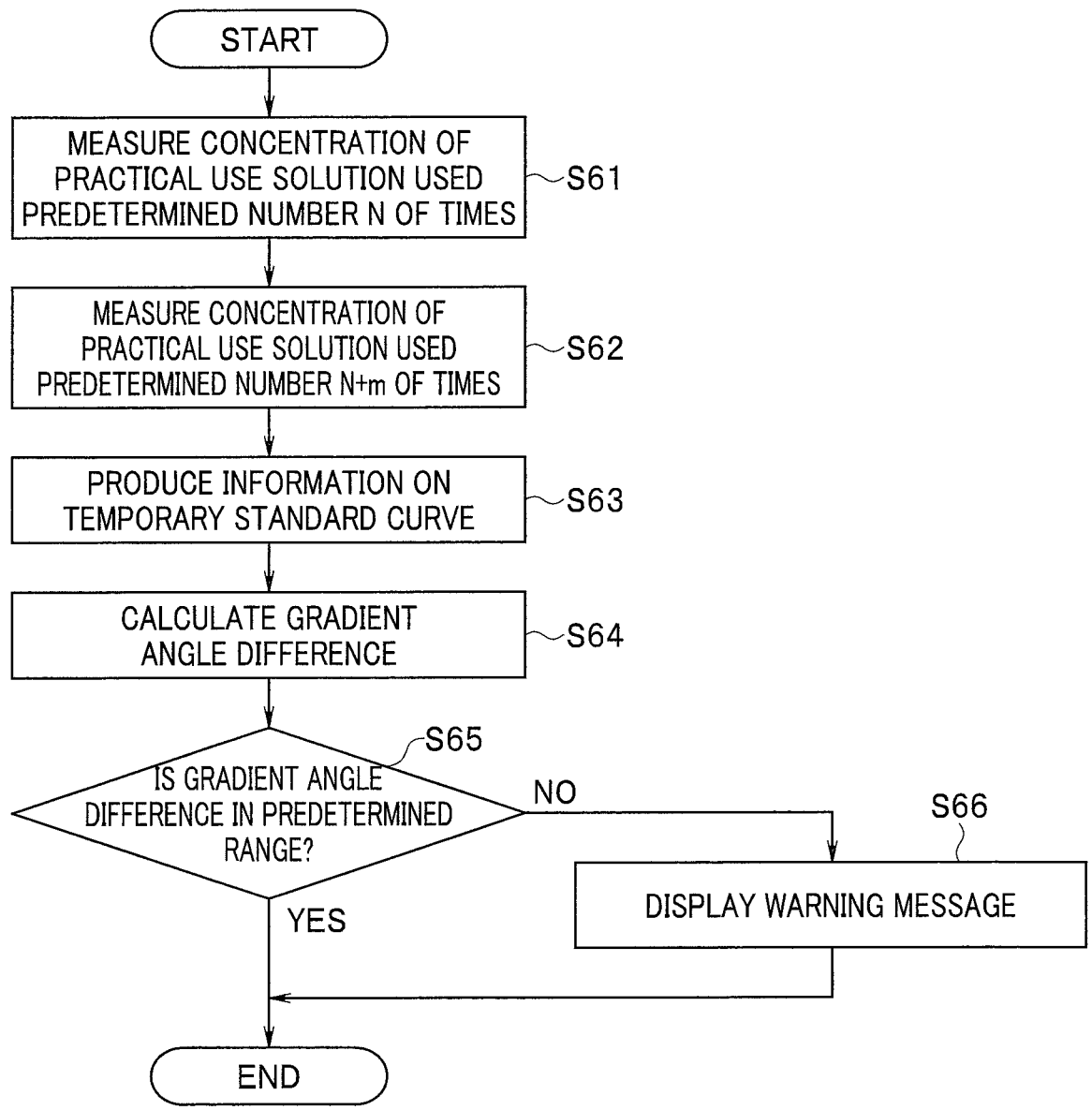
FIG. 12 is a flowchart illustrating a process of a measurement accuracy detection processing at the endoscope reprocessor according to Modification 1 of the third embodiment of the present invention.

FIG. 12 is a flowchart illustrating the process of the measurement accuracy detection processing at the endoscope reprocessor 1 according to Modification 1 of the third embodiment of the present invention. In the description of Modification 1 of the third embodiment, any component same as the component in the third embodiment is denoted by the same reference sign, and description of the component will be omitted.

As illustrated in FIG. 1, the endoscope reprocessor 1 includes the liquid concentrate supply unit 94 and the diluent supply unit 95.

The concentration of practical use solution used the predetermined N of times is measured (S61). First, practical use solution is transferred to the reprocessing basin 31 and used the predetermined N of times. Subsequently, the control unit 101 causes the concentration sensor 97 to measure the concentration of the practical use solution, and acquires a current value as a sensor output value from the concentration sensor 97.

The concentration of the practical use solution used the predetermined number N+m of times is measured (S62). After used the predetermined N of times at S61, the practical use solution is further transferred to the reprocessing basin 31 and used the predetermined number m of times. The control unit 101 causes the concentration sensor 97 to measure the concentration of the practical use solution, and acquires a current value as a sensor output value from the concentration sensor 97.

Processing at S63 to S66 is same as the processing at S53 to S56, and thus description of the processing will be omitted.

Fourth Embodiment

In the first, second, and third embodiments and the modifications of the embodiments, the standard curve production unit 105 produces information on the temporary standard curve Lc connecting two measurement points, but may produce the temporary standard curve Lc based on three or more measurement points.

Figure 13:
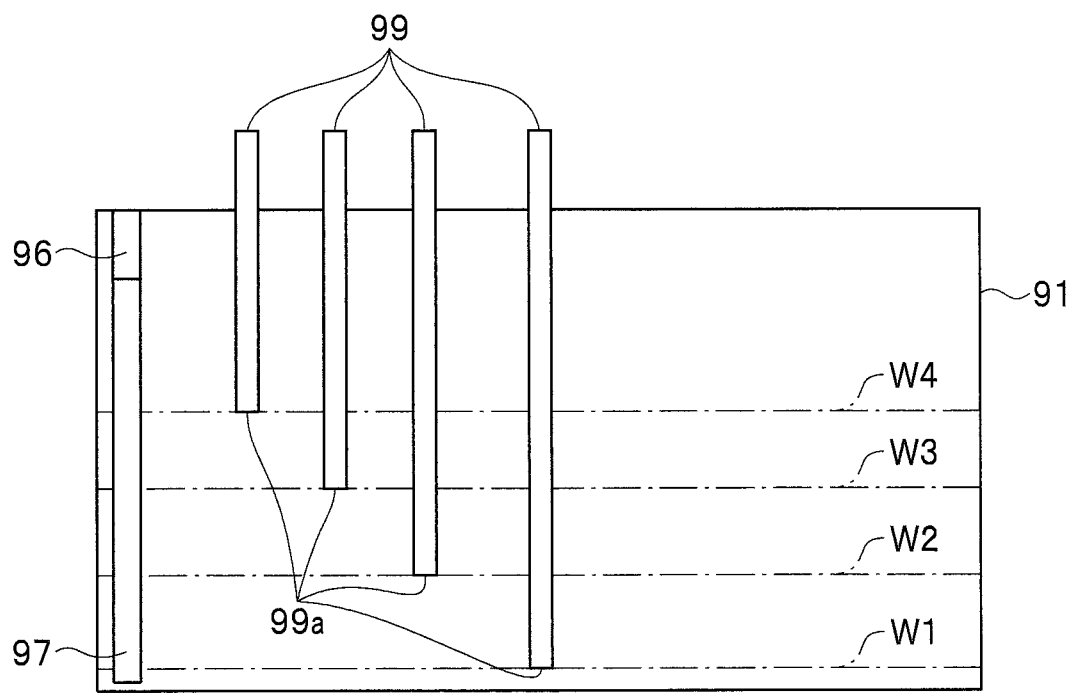
FIG. 13 is an explanatory diagram for description of a configuration of a concentration sensor and a water level sensor in the endoscope reprocessor according to a fourth embodiment of the present invention.
Figure 14:
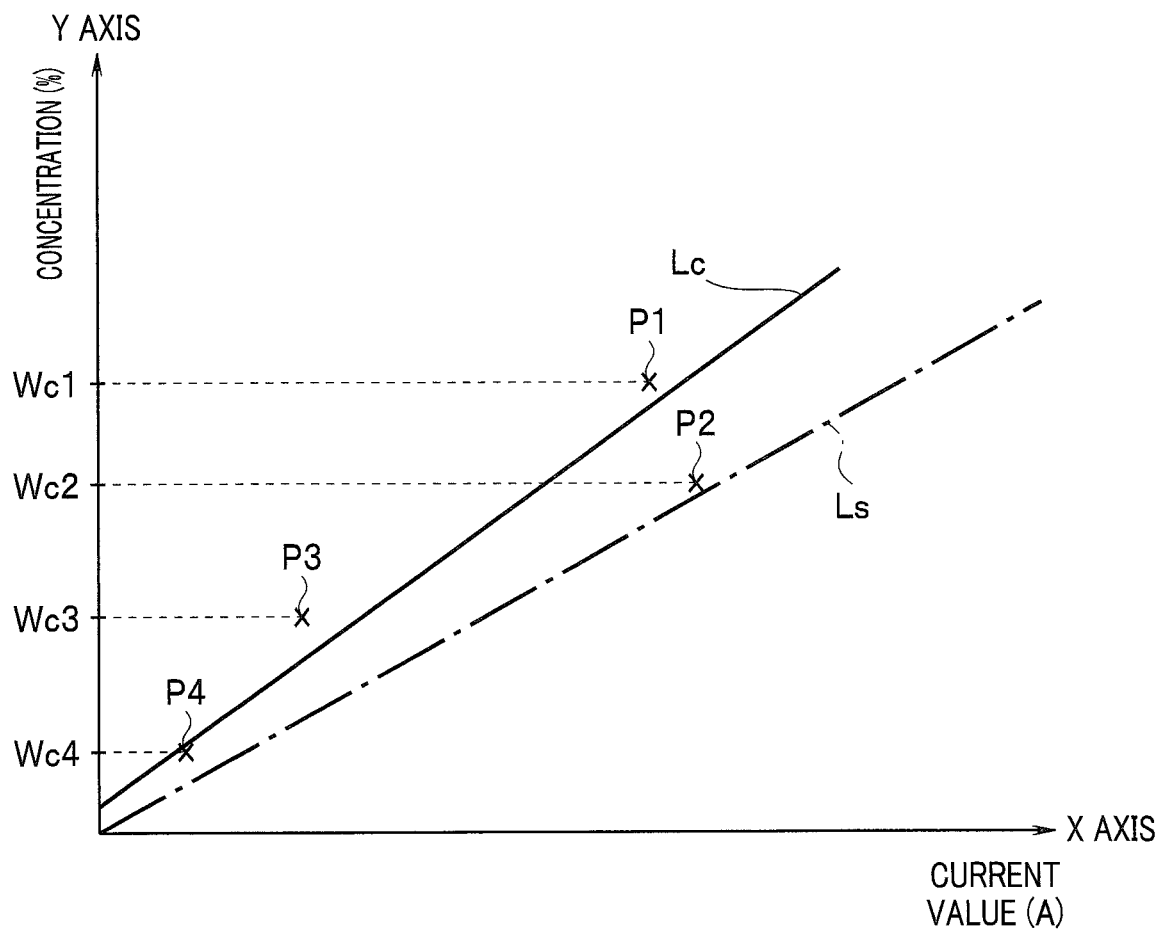
FIG. 14 is an explanatory diagram for description of a temporary standard curve in a measurement accuracy detection processing at the endoscope reprocessor according to the fourth embodiment of the present invention.

FIG. 13 is an explanatory diagram for description of the configuration of the concentration sensor 97 and the water level sensor 99 of the endoscope reprocessor 1 according to a fourth embodiment of the present invention. FIG. 14 is an explanatory diagram for description of the temporary standard curve Lc in the measurement accuracy detection processing at the endoscope reprocessors 1 and 1a according to the fourth embodiment of the present invention. In the description of the fourth embodiment, any component included in the first, second, and third embodiments and the modifications of the embodiments is denoted by the same reference sign, and description of the component will be omitted.

The water level sensor 99 includes a plurality of water level detection units 99a each achieved by, for example, an electrode, and can detect predetermined water levels W1, W2, W3, and W4. When diluent is supplied into the medicinal solution tank 91 from the liquid concentrate supply unit 94 or the diluent supply unit 95, the water level of the medicinal solution tank 91 rises, and the water level sensor 99 sequentially detects the predetermined water level W1, W2, W3, or W4 and outputs a result of the detection to the control unit 101.

Predetermined concentrations Wc1, Wc2, Wc3, and Wc4 in accordance with the predetermined water levels W1, W2, W3, and W4, respectively, are calculated and set in advance based on the supplied amounts of liquid concentrate and the volumes of medicinal solution at the predetermined water levels W1, W2, W3, and W4.

For example, the predetermined concentration Wc1 may be the first concentration, the predetermined concentrations Wc2 and Wc3 may be concentrations in dilution, and the predetermined concentration Wc4 may be the second concentration.

When any of the predetermined water levels W1, W2, W3, and W4 is detected by the water level sensor 99, the control unit 101 acquires a current value as a sensor output value from the concentration sensor 97. The control unit 101 produces information on the temporary standard curve Lc by disposing measurement points P1, P2, P3, and P4 on the XY plane at which the current values as sensor output values are associated with the predetermined concentrations Wc1, Wc2, Wc3, and Wc4 and performing predetermined arithmetic processing by, for example, a least-square method.

According to the above-described fourth embodiment, the endoscope reprocessor 1 can produce information on the temporary standard curve Lc based on three or more measurement points and more reliably detect decrease of the measurement accuracy at the concentration sensor 97.

The water level sensor 99 illustrated in FIG. 13 can detect the four predetermined water levels W1, W2, W3, and W4, but is not limited to four water levels. The water level sensor 99 may be capable of detecting five or more water levels.

In the fourth embodiment, three or more measurement points are used to produce information on the temporary standard curve Lc, but may be used to produce information on the standard curve Ls.

Modification 1 of Fourth Embodiment

The temporary standard curve Lc, which is produced based on measurement points at which the water level is detected by the water level sensor 99 in the fourth embodiment, may be produced based on measurement points including a measurement point at which the water level is zero.

Figure 15:
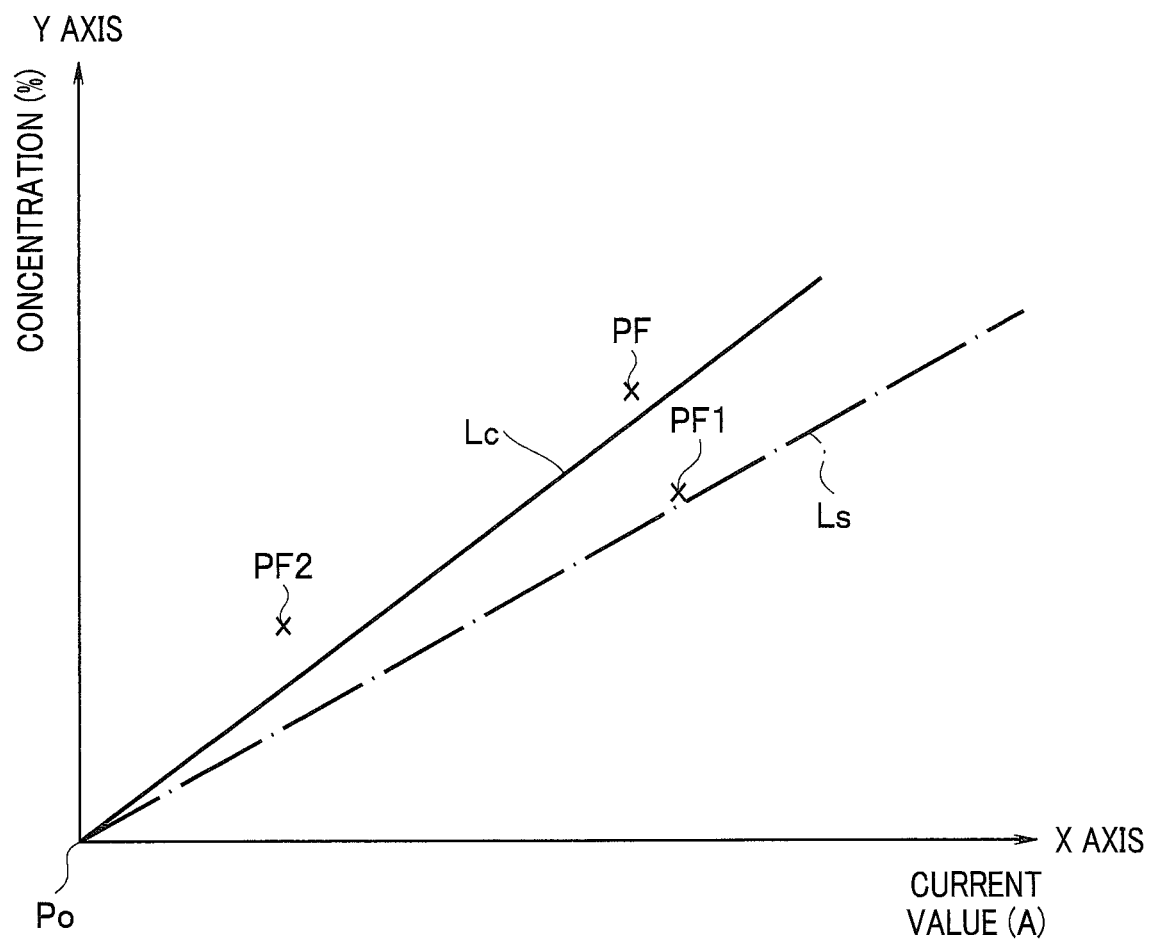
FIG. 15 is an explanatory diagram for description of a temporary standard curve in a measurement accuracy detection processing at the endoscope reprocessor according to Modification 1 of the fourth embodiment of the present invention.

FIG. 15 is an explanatory diagram for description of the temporary standard curve Lc in the measurement accuracy detection processing at the endoscope reprocessors 1 and 1a according to Modification 1 of the fourth embodiment of the present invention.

As illustrated in FIG. 15, the endoscope reprocessors 1 and 1a produce the temporary standard curve Lc based on a measurement point P0 acquired when the water level is zero, a measurement point PF acquired when dilution is completed, and measurement points PF1 and PF2 each acquired after the solution is transferred a predetermined number of times. Although information on the temporary standard curve Lc including the measurement point P0 is produced in Modification 1 of the fourth embodiment, information on the standard curve Ls including the measurement point P0 may be produced.

Fifth Embodiment

In the first, second, third, and fourth embodiments and the modifications of the embodiments, decrease of the measurement accuracy at the concentration sensor 97 is detected based on the temporary standard curve Lc, but may be detected based on a first standard point Pc1 and a second standard point Pc2.

Figure 16:
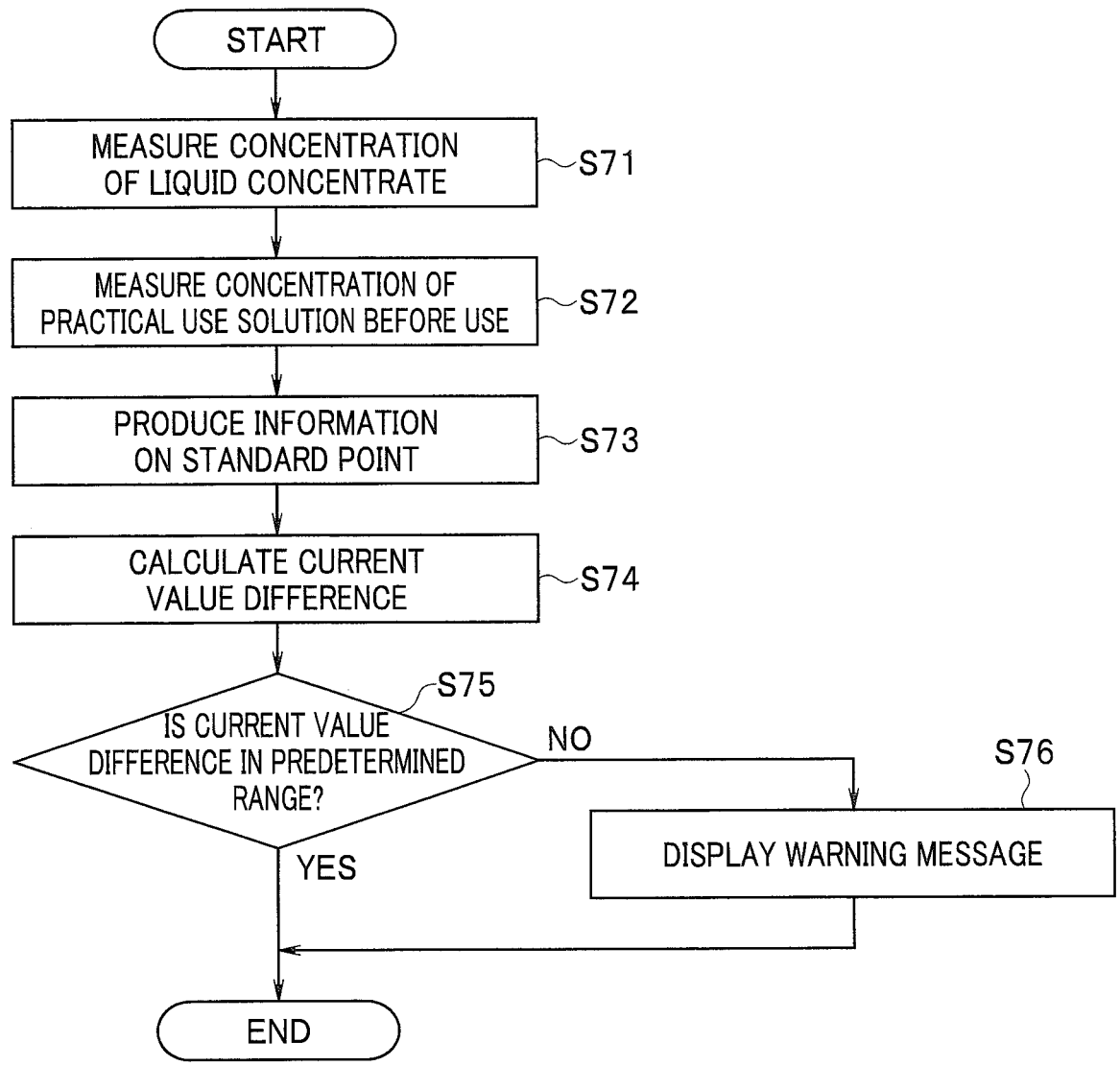
FIG. 16 is a flowchart illustrating a process of the measurement accuracy detection processing at the endoscope reprocessor according to a fifth embodiment of the present invention.
Figure 17:
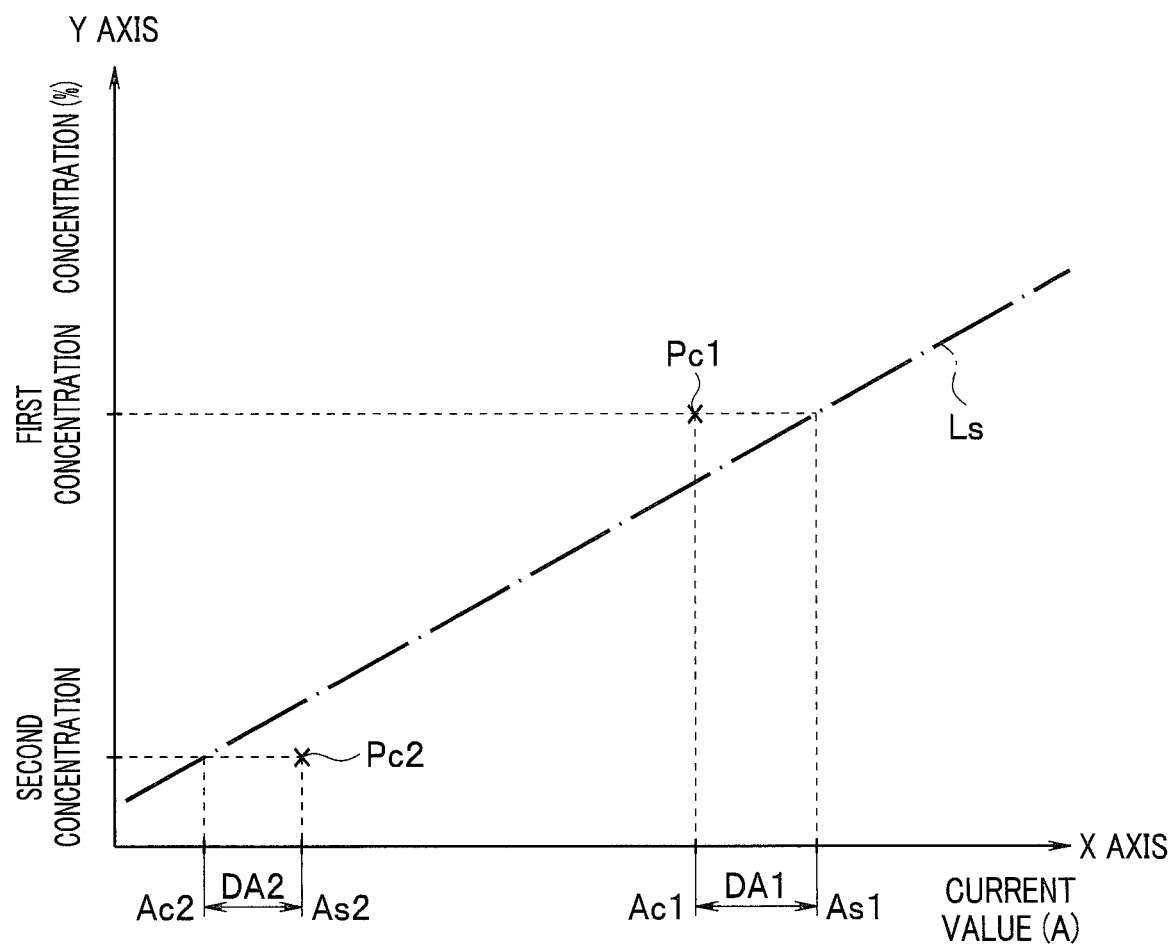
FIG. 17 is an explanatory diagram for description of a current value difference in the measurement accuracy detection processing at the endoscope reprocessor according to the fifth embodiment of the present invention.

FIG. 16 is a flowchart illustrating the process of the measurement accuracy detection processing at the endoscope reprocessor 1 according to a fifth embodiment of the present invention. FIG. 17 is an explanatory diagram for description of the current value differences DA1 and DA2 in the measurement accuracy detection processing at the endoscope reprocessor 1 according to the fifth embodiment of the present invention. In the description of the fifth embodiment, any component included in the first, second, third, and fourth embodiments and the modifications of the embodiments is denoted by the same reference sign, and description of the component will be omitted.

The endoscope reprocessor 1 includes a standard point production unit 109 (indicated by a dashed-double-dotted line in FIG. 1). The standard point production unit 109 produces a standard point by associating the first concentration with a current value at measurement of the concentration of liquid concentrate or associating the second concentration with a current value as a sensor output value at measurement of concentration of practical use solution.

The following describes the measurement accuracy detection processing according to the fifth embodiment. Processing at S71 and S72 may be same as any one of the processing at S1 and S2, the processing at S11 and S12, the processing at S21 and S22, and the processing at S31 and S32, and thus description of the processing will be omitted.

Standard points are produced (S73). The control unit 101 produces, on the XY plane, standard points including the first standard point Pc1 at which the first concentration is associated with a current value as a sensor output value obtained at S71 and the second standard point Pc2 at which the second concentration is associated with a current value as a sensor output value obtained at S72.

Processing at S74 to S76 may be same as the processing at S14 to S16 or the processing at S44 to S46, and thus description of the processing will be omitted.

The processing at S71 to S76 corresponds to the measurement accuracy detection processing according to the fifth embodiment.

The processing at S73 corresponds to processing at the standard point production unit 109 according to the fifth embodiment.

According to the above-described fifth embodiment, the endoscope reprocessor 1 can detect decrease of the measurement accuracy at the concentration sensor 97 based on the first standard point Pc1 and the second standard point Pc2.

Modification 1 of Fifth Embodiment

In the fifth embodiment, the standard point production unit 109 produces standard points by measuring the concentration of liquid concentrate and the concentration of practical use solution, but may produce standard points by measuring the concentration of the examination target solution before use and the concentration of the examination target solution used the predetermined N of times. In the description of Modification 1 of the fifth embodiment, any component same as the component in the fifth embodiment is denoted by the same reference sign, and description of the component will be omitted.

In Modification 1 of the fifth embodiment, the control unit 101 produces standard points by associating the second concentration with a current value as a sensor output value at measurement of concentration of the examination target solution not transferred to the reprocessing basin 31 or associating the third concentration with a current value as a sensor output value at measurement of concentration of the examination target solution transferred to the reprocessing basin 31 the predetermined N of times.

In the fifth embodiment and Modification 1 of the fifth embodiment, each standard point is a measurement point, but may be a predetermined point on the temporary standard curve Lc produced based on a plurality of measurement points, for example, two points or three or more points, through processing by the standard curve production unit 105.

In the embodiments and the modifications, information on the standard curve Ls is produced through the processing at S1 to S3 in the endoscope reprocessor 1, but does not need to be produced by the endoscope reprocessor 1. For example, information on the standard curve Ls may be produced by housing medicinal solution prepared in advance in, for example, a beaker and measuring, by the concentration sensor 97 yet to be attached to the endoscope reprocessor 1, the concentration of the medicinal solution housed in, for example, the beaker.

Standard curve information may be read by the endoscope reprocessors 1 and 1a from the concentration sensor 97 provided with the standard curve information, and may be stored in the standard curve storage unit 104. Alternatively, the concentration sensor 97 may be provided with the standard curve storage unit 104 storing the standard curve information. Alternatively, the standard curve information may be downloaded from a cloud.

In the embodiments and the modifications, the standard curve production unit 105 performs the standard curve production processing by using liquid concentrate, diluent, and practical use solution. Medicinal solution used in the standard curve production processing is not limited to the mixture, but any other medicinal solution is applicable.

In the embodiments and the modifications, information on the standard curve Ls produced through the processing at S1 to S3 is stored in the standard curve storage unit 104 through the processing at S4. However, when a standard curve same as the standard curve Ls of the concentration sensor 97 is already produced, for example, when a standard curve is already produced for another concentration sensor 97 of the same kind, the processing at S1 to S3 may be omitted, and information on the standard curve Ls may be stored in the standard curve storage unit 104 through the processing at S4.

In the embodiments, the standard curve production unit 105, the calculation unit 106, the determination unit 107, the counting unit 108, and the standard point production unit 109 are provided integrally with the control unit 101, but may be provided separately from the control unit 101.

Each "unit" in the present specification conceptually corresponds to each function in the embodiments, and does not necessarily correspond to a particular hardware device or a software routine on a one-on-one basis. Thus, the present specification describes each embodiment by assuming a virtual circuit block (unit) having each function in the embodiments. Steps of each procedure in the present embodiment may be executed in a different order or simultaneously, or may be executed in an order different at each execution, as long as the feature of the procedure is maintained. All or part of the steps of each procedure in the present embodiment may be achieved by hardware.

The present invention is not limited to the above-described embodiments, but may be, for example, changed and modified in various manners without departing from the scope of the present invention.

The present invention provides an endoscope reprocessor including a concentration sensor and capable of detecting any defect of the concentration sensor.

What is claimed is:

1. An endoscope reprocessor comprising:
   a concentration measurement chamber in which practical use solution at a predetermined concentration is housed;
   a liquid concentrate supply unit comprising a medicinal solution bottle in which liquid concentrate containing an examination object at a first concentration is housed, and a liquid concentrate supply conduit through which the medicinal solution bottle and the concentration measurement chamber are communicated with each other;
   a diluent supply unit comprising a conduit communicatively connected with the concentration measurement chamber and a water supply conduit through which diluent flows, and an electromagnetic valve provided on the conduit, the diluent supply unit being configured to supply the diluent to the concentration measurement chamber to dilute the liquid concentrate and prepare the practical use solution containing the examination object at a second concentration;
   a concentration sensor configured to be in contact with the liquid concentrate and the practical use solution;
   a memory configured to store information on a standard curve of the concentration sensor; and
   a controller comprising hardware, the controller being configured to:
      produce information on a temporary standard curve based on a first point at which the first concentration is associated with a sensor output value at measurement of concentration of the liquid concentrate and a second point at which the second concentration is associated with a sensor output value at measurement of concentration of the practical use solution,
      calculate a deviation degree between the standard curve and the temporary standard curve, and
      determine whether the temporary standard curve is valid from the deviation degree.

2. The endoscope reprocessor according to claim 1, wherein the examination object is peracetic acid.

3. The endoscope reprocessor according to claim 1, wherein the deviation degree is a current value difference between the standard curve and the temporary standard curve at a predetermined concentration.

4. The endoscope reprocessor according to claim 1, wherein the deviation degree is a gradient angle difference between the standard curve and the temporary standard curve.

5. The endoscope reprocessor according to claim 1, wherein the deviation degree is an area of a region partitioned by the standard curve and the temporary standard curve in a predetermined current value range.

6. An endoscope reprocessor comprising:
   a concentration measurement chamber in which practical use solution at a predetermined concentration is housed;
   a liquid concentrate supply unit comprising a medicinal solution bottle in which liquid concentrate containing an examination object at a first concentration, is housed, and a liquid concentrate supply conduit through which the medicinal solution bottle and the concentration measurement chamber are communicated with each other;
   a diluent supply unit comprising a conduit communicatively connected with the concentration measurement chamber and a water supply conduit through which diluent flows, and an electromagnetic valve provided on the conduit, the diluent supply unit being configured to supply the diluent to the concentration measurement chamber to dilute the liquid concentrate and prepare the practical use solution containing the examination object at a second concentration;
   a concentration sensor configured to be in contact with the liquid concentrate and the practical use solution;
   a reprocessing basin in which an endoscope is disposed;
   a first solution transfer unit comprising a medicinal solution conduit that couples the concentration measurement chamber and the reprocessing basin, and a medicinal solution pump provided on the medicinal solution conduit;
   a second solution transfer unit comprising a medicinal solution recovery conduit through which the reprocessing basin and the concentration measurement chamber are communicated with each other, and a medicinal solution recovery valve provided on the medicinal solution recovery conduit;
   a counter configured to count the number of times that the practical use solution is transferred to the reprocessing basin;
   a memory configured to store information on a standard curve of the concentration sensor; and
   a controller comprising hardware, the controller being configured to:
      produce information on a temporary standard curve based on at least one of a first point at which the first concentration is associated with a sensor output value at measurement of concentration of the liquid concentrate and a second point at which the second concentration is associated with a sensor output value at measurement of concentration of the practical use solution, and based on a third point at which a third concentration obtained by subtracting $N \times x$ ($x$ is a positive number) from the second concentration is associated with a sensor output value at measurement of concentration of the practical use solution transferred to the reprocessing basin N times (N is equal to or larger than one), calculate a deviation degree between the standard curve and the temporary standard curve, and determine whether the temporary standard curve is valid from the deviation degree.

7. The endoscope reprocessor according to claim 6, wherein the controller produces the temporary standard curve based on three or more measurement points.

8. An endoscope reprocessor comprising:

a concentration measurement chamber in which examination target solution at a predetermined concentration is housed;

an examination target solution supply unit connected to the concentration measurement chamber, and comprising a conduit through which the examination target solution flows;

a concentration sensor configured to be in contact with the examination target solution;

a reprocessing basin in which an endoscope is disposed;

a first solution transfer unit comprising a medicinal solution conduit that couples the concentration measurement chamber and the reprocessing basin, and a medicinal solution pump provided on the medicinal solution conduit;

a second solution transfer unit comprising a medicinal solution recovery conduit through which the reprocessing basin and the concentration measurement chamber are communicated with each other, and a medicinal solution recovery valve provided on the medicinal solution recovery conduit;

a counter configured to count the number of times that the examination target solution is transferred to the reprocessing basin;

a memory configured to store information on a standard curve of the concentration sensor; and a controller comprising hardware, the controller being configured to:

produce information on a temporary standard curve based on a first point at which a first concentration is associated with a sensor output value at measurement of concentration of the examination target solution transferred to the reprocessing basin N times (N is equal to or larger than zero) and a second point at which a second concentration obtained by subtracting m×y (y is a positive number) from the first concentration is associated with a sensor output value at measurement of concentration of the examination target solution transferred to the reprocessing basin N+m times (m is equal to or larger than one), calculate a deviation degree between the standard curve and the temporary standard curve, and determine whether the temporary standard curve is valid based on the deviation degree.

9. The endoscope reprocessor according to claim 8, wherein the controller produces the temporary standard curve based on three or more measurement points.

10. The endoscope reprocessor according to claim 8, wherein the examination target solution is liquid containing peracetic acid.

* * * * *